United States Patent
Orr et al.

(10) Patent No.: US 10,435,681 B2
(45) Date of Patent: *Oct. 8, 2019

(54) COMPOUNDS AND METHODS FOR STABILIZING THROMBIN ACTIVITY

(71) Applicant: Omrix Biopharmaceuticals Ltd., Rehovot (IL)

(72) Inventors: Nadav Orr, Mazkeret Batia (IL); Yair Pilpel, Rehovot (IL); Sivan Doron, Moshav Arugot (IL)

(73) Assignee: Omrix Biopharmaceuticals Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/144,262

(22) Filed: Sep. 27, 2018

(65) Prior Publication Data
US 2019/0017040 A1    Jan. 17, 2019

Related U.S. Application Data

(62) Division of application No. 14/519,552, filed on Oct. 21, 2014, now Pat. No. 10,131,896.

(60) Provisional application No. 61/896,674, filed on Oct. 29, 2013.

(30) Foreign Application Priority Data

Oct. 29, 2013 (IL) .......................................... 229134

(51) Int. Cl.
| C07K 16/00 | (2006.01) |
| C12N 9/74 | (2006.01) |
| C12Q 1/56 | (2006.01) |
| A61K 38/43 | (2006.01) |
| C07K 7/00 | (2006.01) |

(52) U.S. Cl.
CPC ............ *C12N 9/6429* (2013.01); *A61K 38/43* (2013.01); *C07K 7/00* (2013.01); *C12Q 1/56* (2013.01); *C12Y 304/21005* (2013.01); *G01N 2500/04* (2013.01)

(58) Field of Classification Search
None
See application file for complete search history.

(56) References Cited

U.S. PATENT DOCUMENTS

| 4,409,334 | A | 10/1983 | Lill et al. |
| 5,218,088 | A | 6/1993 | Gorenstein et al. |
| 5,580,560 | A | 12/1996 | Nicolaisen et al. |
| 5,831,005 | A | 11/1998 | Zuckerman et al. |
| 5,877,278 | A | 3/1999 | Zuckerman et al. |
| 5,977,301 | A | 11/1999 | Zuckerman et al. |
| 6,423,493 | B1 | 7/2002 | Gorenstein et al. |
| 7,189,690 | B2 | 3/2007 | Rosen et al. |
| 7,351,561 | B2 | 4/2008 | Metzner et al. |
| 7,745,391 | B2* | 6/2010 | Mintz ...................... G06F 19/24 514/19.3 |
| 8,394,372 | B2 | 3/2013 | Anderson et al. |
| 8,435,748 | B2* | 5/2013 | Kim ........................ C07K 16/36 435/7.1 |
| 9,494,601 | B2* | 11/2016 | McKnight .............. C07K 16/18 |
| 9,598,687 | B2* | 3/2017 | Hunter ................. C07K 14/745 |
| 9,658,236 | B2* | 5/2017 | McKnight .............. C07K 16/18 |
| 2004/0053372 | A1 | 3/2004 | Pelzer et al. |
| 2009/0117578 | A1 | 5/2009 | Metz et al. |
| 2009/0136474 | A1 | 5/2009 | Anderson et al. |

FOREIGN PATENT DOCUMENTS

| EP | 0478827 B1 | 4/1992 |
| EP | 0277096 B1 | 7/1992 |
| WO | WO 2007/035143 | 3/2007 |
| WO | WO 2008/157304 | 12/2008 |
| WO | WO 2013/006550 A1 | 1/2013 |

OTHER PUBLICATIONS

Bah, A., et al., "Stabilization of the E* Form Turns Thrombin into an Anticoagulant" J Biol Chem. (2009) 24; vol. 284, Issue 30 pp. 20034-20040.
Chang, J.-Y. "The structures and proteolytic specificities of autolysed human thrombin" Biochem J. (1986) vol. 240 pp. 797-802.
Krishnaswamy, S. "The transition of prothrombin to thrombin" J. Thromb. Haemost. (Jun. 2013)vol. 11, Suppl. 1 pp. 265-276.
Marino, F. "Engineering Thrombin for Selective Specificity toward Protein C and PAR1" J Biol Chem. (2010) vol. 285, No. 25 pp. 19145-19152.
Masch, A., et al., 'Antibody Signatures Defined by High-Content Peptide Microarray Analysis' Methods Mol. Biol. (2010) vol. 669 pp. 161-172.
Nguyen, J.T. et al. 'Improving SH3 domain ligand selectivity using a non-natural scaffold' Chem Biol. (2000) vol. 7, No. 7 pp. 463-473.
Panse, S., et al. 'Profiling of generic anti-phosphopeptide antibodies and kinases with peptide microarrays using radioactive and fluorescence-based assays' Mol Divers (2004) 8:291-299.
Pozzi, N., et al., "Rigidification of the autolysis loop enhances Na+ binding to thrombin" Biophys Chem. (2011) 159(1) pp. 6-13.
Rydel, T.J., et al "Crystallographic structure of human gamma-thrombin" J Biol Chem. (1994) 269(35) pp. 22000-22006.
Simon, R.J. et al. 'Peptoids: A modular approach to drug delivery' Proc. Natl. Acad. Sci. USA (1992) 89(20) pp. 9367-9371.

(Continued)

*Primary Examiner* — Hope A Robinson

(74) *Attorney, Agent, or Firm* — David R. Crichton

(57) ABSTRACT

The present invention is directed to compounds useful in stabilizing thrombin activity, thrombin compositions comprising the compounds, methods of using the compounds and methods of identifying compounds capable of stabilizing thrombin activity. The compounds are preferably isolated peptides comprising or interacting with the gamma loop of thrombin.

10 Claims, 7 Drawing Sheets

Specification includes a Sequence Listing.

(56) References Cited

OTHER PUBLICATIONS

Stuart and Young (1984), "Solid Phase Peptide Synthesis," Solid Phase Peptide Synthesis, Methods Enzymol., Second Edition, Pierce Chemical Company, 289, Academic Press, Inc., NY (1997).

Wenschuh, H., et al. 'Coherent membrane supports for parallel microsynthesis and screening of bioactive peptides' Biopolymers (2000) 55 pp. 188-206.

Yang, L. et al "Heparin-activated antithrombin interacts with the autolysis loop of target coagulation proteases" Blood (2004) 104(6) pp. 1753-1759.

Geneseq 'Human Prothrombin precursor peptide, Seq ID:1529' XP002737078, retrieved from EBI accession No. GSP: AWV25352, Database accession No. AWV25352 sequence.

Suzuki, K. et al 'A Thrombin-based Peptide Corresponding to the Sequence of the Thombomodulin-binding Site Blocks the Procoagulant Activities of Thrombin' The Journal of Biological Chemistry (1991) vol. 266, No. 28 pp. 18498-18501.

International Preliminary Report on Patentability re: PCT/IL2014/000056 dated May 3, 2016.

International Search Report re: PCT/IL2014/000056 dated Mar. 26, 2015.

Parry, Marina A.A., "Evidence for Common Structural Changes in Thrombin Induced by Active-Site or Exosite Binding", Biochem Journal, vol. 290, pp. 665-670 (1993).

* cited by examiner

*NH2*             LYS-GLU-THR-TRP-THR-ALA-ASN-VAL-GLY-LYS          (SEQ ID NO:1)

*NH2*    GLY-ASN-LEU-[LYS-GLU-THR-TRP-THR-ALA-ASN-VAL-GLY-LYS]-GLY-GLN-PRO-SER (SEQ ID NO:2)

COMPOUNDS AND METHODS FOR STABILIZING THROMBIN ACTIVITY

CROSS-REFERENCE TO RELATED APPLICATION

This application is a divisional application of co-pending U.S. application Ser. No. 14/519,552 filed on Oct. 21, 2014, the complete disclosure of which is hereby incorporated herein by reference for all purposes.

SEQUENCE LISTING

The instant application contains a Sequence Listing, which is submitted concomitantly with this application via EFS-Web in ASCII format and is hereby incorporated by reference in its entirety. Said ASCII copy, created on Oct. 7, 2013, is named "sequencelisting" and is 4 kilobytes in size.

FIELD OF THE INVENTION

Provided herein are compounds, compositions and formulations comprising same and methods useful for stabilizing thrombin activity and extending thrombin's shelf-life. In particular, disclosed herein are isolated peptides comprising the amino acid sequence of the thrombin gamma loop and isolated peptides that are capable of interacting with the gamma loop of the thrombin, compositions, formulations, and methods of use therefore to stabilize thrombin activity in a liquid thrombin formulation. Further provided is a method to identify compounds capable of stabilizing thrombin activity.

BACKGROUND

Thrombin is a serine protease which serves as an active component in several hemostasis products. For example, fibrin sealants typically comprise a fibrinogen component and a thrombin component. When both components are mixed (e.g. when applied to a bleeding wound or surgical incision) thrombin cleaves fibrinogen and a fibrin polymer is formed. Concentrated purified thrombin in liquid form displays a reduction in activity during prolonged storage, mostly as a result of autolysis.

Hemostatic formulations containing liquid thrombin have special handling requirements in order to maintain thrombin's biologic activity and prevent autolytic degradation. For example, a liquid thrombin formulation requires refrigeration or the addition of protease inhibitors to maintain shelf-life stability. In the clinic, refrigeration is not always feasible, and promiscuous protease inhibitors may adversely affect the activity of thrombin.

Thrombin may be made into a lyophilized medical preparation, which is used after dissolving at the time of use. However, liquid preparations are advantageous as compared with the lyophilized preparations in that they can be easily administered without the additional step of dissolving in a solvent prior to use.

Other known compositions and methods for stabilizing thrombin are unsatisfactory and include the following: inclusion of various non-specific components (e.g. bulk carrier proteins such as albumins, different stabilizing sugars, general protease inhibitors etc.); formulation of the thrombin with inhibitors of thrombin activity, which although may be efficient, may also inactivate or inhibit the thrombin during use thereby reducing its effectiveness. In order to avoid or reduce inhibition, in use, it may be needed prior to use to dilute the inhibitor and therefore the thrombin. Formulation of a low dose thrombin, necessitates administration of larger amounts of the formulation.

International Patent Application Publication No. WO2008157304 discloses methods for stabilizing thrombin solutions with a preservative selected from benzyl alcohol or chlorobutanol and sucrose. Additional Patent Publications provide compositions comprising thrombin and non-specific inhibitors, and therefore, cannot effectively counter the thrombin-thrombin autolysis effect. For example, U.S. Pat. No. 4,409,334 discloses a stabilized thrombin preparation in solid or dissolved form comprising thrombin and as a stabilizer serum albumin together with at least one protease inhibitor which does not inhibit thrombin itself and at least one hexaligand chelate former.

European Patent No. EP0277096 B1 provides a stable thrombin composition containing purified thrombin, a polyol, and a buffer which contains either acetate or phosphate ions, wherein the preparation has a pH of about 5.0 to about 6.0.

European Patent No. EP 0478827 B1 provides a stable thrombin composition which includes a mixture of three stabilizers: HEPES-buffer, thiomersal, gelatin obtained by partial hydrolysis of collagen, and optionally Polybrene.

U.S. Pat. No. 7,351,561 discloses a stable thrombin preparation comprising thrombin and benzamidine or p-aminobenzamidine as stabilizer, and further including calcium chloride or sodium chloride as stabilizer, at least one buffer substance, and at least one of histidine, mannitol, sodium succinate, sodium lactate or arginine.

US Patent Application Publication No. 20090136474 (U.S. Pat. No. 8,394,372) provides a stabilized serine protease composition which comprises a serine protease; a reversible inhibitor of said serine protease (e.g. benzamidine, N,N-diethylethylenediamine, aminobenzamidine); and a stabilizing agent (e.g. 3-(N-morpholino)propane sulfonic acid). Non-patent literature describing various aspects of thrombin include: Pozzi N, et al., (2011) "Rigidification of the autolysis loop enhances Na(+) binding to thrombin" (Biophys Chem. 159(1):6-13); Marino, F. (2010) "Engineering thrombin for selective specificity toward protein C and PAR1" (J Biol Chem. 285(25):19145-52); Bah A, et al., (2009) "Stabilization of the E* form turns thrombin into an anticoagulant" (J Biol Chem. 24;284(30):20034-40); Yang L (2004) "Heparin-activated antithrombin interacts with the autolysis loop of target coagulation proteases" (Blood. 104 (6):1753-9); and Rydel T J, et al (1994) "Crystallographic structure of human gamma-thrombin" (J Biol Chem. 269 (35):22000-6).

Therefore, there remains a need for specific compounds useful to stabilize thrombin from autolytic degradation while retaining its biological activity. Preferably, the compounds may be used with a concentrated liquid thrombin formulation.

SUMMARY OF THE INVENTION

Provided herein is a compound which has the exceptional ability to stabilize thrombin activity. The compound is capable of stabilizing activity of thrombin in a liquid formulation and is useful in extending the shelf-life of thrombin. Without wishing to be bound to theory, the compound inhibits, fully or partially, thrombin autolysis, while preserving thrombin activity toward its heterologous substrates, including fibrinogen.

One advantage is that the stabilized thrombin comprising the compound can be used directly for activating fibrinogen.

The stabilized thrombin can be used without dilution and/or without removing the compound from the solution.

The compound is further beneficial in that it is potent and can be used in low concentrations, and thus, is readily diluted upon addition of the stabilized thrombin formulation to a substrate. Further provided is a composition or a formulation comprising the compound, methods of using the compound and methods of identifying such compound.

In one aspect, provided herein is a compound capable of stabilizing the activity of thrombin in a liquid formulation, wherein the compound is selected from the group consisting of an isolated peptide which includes the amino acid sequence of the thrombin gamma loop, a derivative or salt thereof and a thrombin gamma loop interacting molecule, a derivative or salt thereof. In some embodiments, the amino acid sequence of the thrombin gamma loop includes an amino acid sequence KETWTANVGK set forth in SEQ ID NO:1.

In some embodiments, the compound is an isolated peptide comprising the gamma loop peptide, a derivative or salt of such peptide or of such derivative.

In some embodiments, the compound is an isolated gamma loop peptide, a derivative or salt of such peptide or of such derivative.

In some embodiments, the peptide is linear or cyclized.

In some embodiments, the isolated gamma loop peptide is linear.

In some embodiments, the linear isolated gamma loop peptide includes an amino acid sequence set forth in SEQ ID NO:1, a derivative or a salt thereof.

In preferred embodiments, the linear isolated gamma loop peptide, derivative or a salt thereof has an amino acid sequence set forth in SEQ ID NO:1.

In some embodiments, the isolated peptide comprises the thrombin gamma loop sequence and one or more amino acids flanking the gamma loop.

In some embodiments the isolated peptide includes 3-4 amino acids at each terminus of the peptide. The amino acids can be, for example, the amino acids that are naturally adjacent to the thrombin gamma loop amino acid sequence. In various embodiments, the isolated peptide has an amino acid sequence set forth in SEQ ID NO:2 (GNLKETWTANVGKGQPS).

In some embodiments, the isolated gamma loop peptide is cyclized.

In some embodiments, the cyclized isolated gamma loop peptide includes an amino acid sequence set forth in SEQ ID NO:1. In preferred embodiments, the cyclized isolated peptide includes a cysteine residue at both termini of the gamma loop amino acid sequence and has an amino acid sequence set forth in SEQ ID NO:3 (CKETWTANVGKC).

In some embodiments, the compound is a thrombin gamma loop interacting molecule, a derivative or salt thereof.

In various embodiments, the interacting molecule is selected from an isolated interacting peptide or derivative thereof, an isolated antibody or antibody fragment thereof, a nucleotide aptamer or a peptide aptamer; or a salt of such a molecule. In preferred embodiments, the interacting molecule is an isolated interacting peptide, or a derivative or salt thereof.

In various embodiments, the isolated interacting peptide is an isolated thrombin peptide which does not include the gamma loop peptide of thrombin, the amino acid sequence of which is derived from the linear thrombin amino acid sequence or from a non-linear, surface facing, folded amino acid sequence of thrombin. For example, the amino acid sequences of the thrombin peptides can be based on the three dimensional structure of thrombin and not necessarily include a primary sequence of thrombin polypeptide. In some embodiments, the isolated thrombin peptide includes an amino acid sequence of SEQ ID NOS:7, 9, 10 or 11. In some embodiments, the isolated thrombin peptide has an amino acid sequence of SEQ ID NOS:7, 9, 10 or 11. In one embodiment, the isolated thrombin peptide, derivative or salt thereof is a linear peptide. In another embodiment, the isolated thrombin peptide derivative or salt thereof is cyclic. In some embodiments, the cyclic thrombin peptide has an amino acid sequence set forth in any one of SEQ ID NOS:7, 9, 10 or 11, and a cysteine residue at each of the amino and carboxy termini.

In various embodiments, the isolated interacting peptide, derivative or salt thereof is obtained from a random peptide library. In some embodiments, the random isolated interacting peptide includes an amino acid sequence of SEQ ID NOS:12 or 13. In one embodiment, the random isolated interacting peptide is a linear peptide. In some embodiments, the random isolated interacting peptide has an amino acid sequence of SEQ ID NOS:12 or 13. In another embodiment, the random isolated interacting peptide is a cyclic peptide. In some embodiments, the cyclic peptide includes an amino acid sequence set forth in any one of SEQ ID NOS:12 or 13, and a cysteine residue at each of the amino and carboxy termini.

In a second aspect, provided herein is a composition comprising a compound capable of stabilizing the activity of thrombin in a liquid thrombin formulation, wherein the compound is selected from an isolated peptide comprising the amino acid sequence of the thrombin gamma loop, a derivative or salt thereof, and a thrombin gamma loop interacting molecule, a derivative or salt thereof. In some embodiments, the compound is present in the composition in an amount effective to stabilize thrombin activity, for example, to inhibit thrombin autolysis without significantly compromising thrombin biological activity; and a pharmacologically acceptable excipient. In some embodiments, the thrombin biological activity comprises cleavage of fibrinogen to fibrin.

In another aspect, provided herein is a thrombin formulation comprising thrombin, a compound capable of stabilizing the activity of thrombin in the formulation, wherein the compound is selected from an isolated peptide comprising the amino acid sequence of the thrombin gamma loop, a derivative or salt thereof, and a thrombin gamma loop interacting molecule, a derivative or salt thereof; and a pharmacologically acceptable excipient.

In some embodiments, the formulation or composition includes thrombin with a thrombin activity of about 1 IU/ml to 10,000 IU/ml, of about 10 IU/ml to 5,000 IU/ml or preferably of about 10 IU/ml to 1,000 IU/ml.

In preferred embodiments of the formulation or composition, the compound is an isolated peptide, a derivative or salt of such peptide or of such derivative.

In some embodiments, the interacting molecule is a thrombin derived peptide or is obtained from a random peptide library.

In some embodiments, the compound is a thrombin derived peptide.

In some embodiments, the compound, e.g. peptide, is present in the composition or formulation at a concentration of about 0.01 mM to about 20 mM, about 0.01 mM to about 1 mM, about 0.1 mM to about 1 mM, about 0. 1 mM to about 0.5 mM, or about 0.5 mM.

Within one embodiment, the compound, composition or formulation are contained in a sealed container having a label affixed to an exterior surface thereof. In some embodiments, the formulation or composition is prepared for use as a fibrin sealant component.

In another aspect, the invention features a kit containing an effective amount of a compound disclosed herein, and directions for using the compound to stabilize thrombin in a liquid formulation. In preferred embodiments, the compound is an isolated peptide, a derivative or salt of such peptide or of such derivative.

In yet another aspect, provided is a method of stabilizing thrombin activity, comprising contacting the thrombin with an isolated peptide comprising the amino acid sequence of the thrombin gamma loop, a derivative or salt thereof or with a molecule that interacts with the gamma loop of the thrombin, in an amount effective to stabilize thrombin activity. In some embodiments, stabilizing thrombin activity comprises inhibiting thrombin autolysis without significantly compromising its biological activity.

In yet another aspect, provided is a method of stabilizing thrombin activity, comprising contacting the thrombin with a compound or the composition disclosed herein.

In another aspect provided herein is a method for screening for a compound capable of stabilizing the activity of thrombin in liquid form, comprising
  a) providing an isolated peptide comprising the amino acid sequence of the thrombin gamma loop;
  b) providing a set of test compounds;
  c) contacting the isolated peptide of (a) with the set of test compounds of (b); and
  d) Identifying one or more test compounds, which bind to the peptide of a).
  whereby the binding indicates a potential compound for use in stabilizing thrombin activity.

In some embodiments, the method further includes the step of isolating the one or more compounds identified in step (d).

In another aspect provided herein is a method for screening for a compound capable of stabilizing the activity of thrombin in liquid form, comprising
  a) providing an isolated peptide comprising the amino acid sequence of the thrombin gamma loop bound to a solid phase;
  b) providing a gamma loop sequence;
  c) providing a set of test labelled compounds;
  d) contacting the isolated peptide of (a) with the set of test compounds of (c) in the presence and absence of the gamma loop sequence of b);
  e) measuring the level of labelled test compound bound to the solid phase in the presence and absence of the gamma loop sequence whereby a substantially unaltered label level in the presence and absence of the gamma loop sequence is indicative that the compound is a candidate for stabilizing thrombin activity.

The labelling can be fluorescent, radioactive labelling or any other labelling known in the art.

In some embodiments, the method further includes the step of testing the one or more identified or candidate compound(s) for their effect in stabilizing the activity of thrombin in liquid form.

In some embodiments, the method further includes the step of testing the one or more identified or candidate compounds for A-their effect in stabilizing the activity of thrombin in liquid form and B-minimal or no inhibition of the peptide on activity towards heterologous substrates e.g. fibrinogen.

In some embodiments of the method, the thrombin gamma loop includes an amino acid sequence set forth in SEQ ID NO:1. In various embodiments, the set of test compounds is obtained from a random peptide library, a chemical compound library, an antibody library, a peptide phage display library, an aptamer library, and the like. In some embodiments, the compound is safe and non-immunogenic.

In some embodiments, the compound is an isolated peptide. In some embodiments, the peptide is synthesized chemically or recombinantly. In various embodiments, provided is a recombinant peptide encoded by an isolated nucleic acid sequence. In some embodiments, the peptide comprises an amino acid sequence set forth in any one of SEQ ID NOS: 1-3, 7 or 9-13.

Provided herein is an isolated nucleic acid sequence encoding the peptide disclosed herein and a vector comprising the nucleic acid sequence encoding such peptide, operatively linked to a promoter element. Further provided is a host cell comprising such vector. The DNA sequence can be extrapolated using the standard genetic code (for example, Lehninger, A. "Principles of Biochemistry").

These and other aspects and embodiments of the invention will become evident upon reference to the following detailed description of the invention and the figures.

BRIEF DESCRIPTION OF THE FIGURES

FIG. 3A is a graph showing stabilization level of thrombin (as shown by measuring % of remaining activity) with random peptides capable of binding the gamma loop. Rnd316 (SEQ IDN NO:12) is listed in the FIG. as Random1. Rnd155 (SEQ IDN NO:13) is listed in the FIG. as Random2.

FIG. 3B is a graph showing stabilization of liquid thrombin (as shown by measuring % of remaining activity) using gamma peptides, both a linear peptide (SEQ ID NO: 2) and a peptide cyclized via intramolecular S-S bonding ("CS"; SEQ ID NO:3).

FIG. 3C is a graph showing stabilization level of thrombin activity (as % of remaining activity) using cyclized mutant gamma loop peptide (SEQ ID NO: 4 [AL-cyc_E03N], SEQ ID NO: 5 [AL-cyc_N08Y] and SEQ ID NO: 6 [AL-cyc_G10L]).

FIG. 3D shows destabilization level of thrombin activity (as % of remaining activity) using the thrombin derived peptide Thr-111 (SEQ ID NO:8).

FIG. 3E is a graph showing stabilization level of thrombin activity (as % of remaining activity) using thrombin derived peptide Thr-069 (SEQ ID NO:7).

FIG. 3F is a graph showing stabilization level of thrombin activity (as % of remaining activity) using linearized peptides in which Cysteine residues have been replaced to Serine (SEQ ID NO: 9 [Thr_031_CS], SEQ ID NO: 10 [Thr_032_CS] and SEQ ID NO: 11 [Thr_136_CS]).

DETAILED DESCRIPTION OF THE INVENTION

Figure 1:
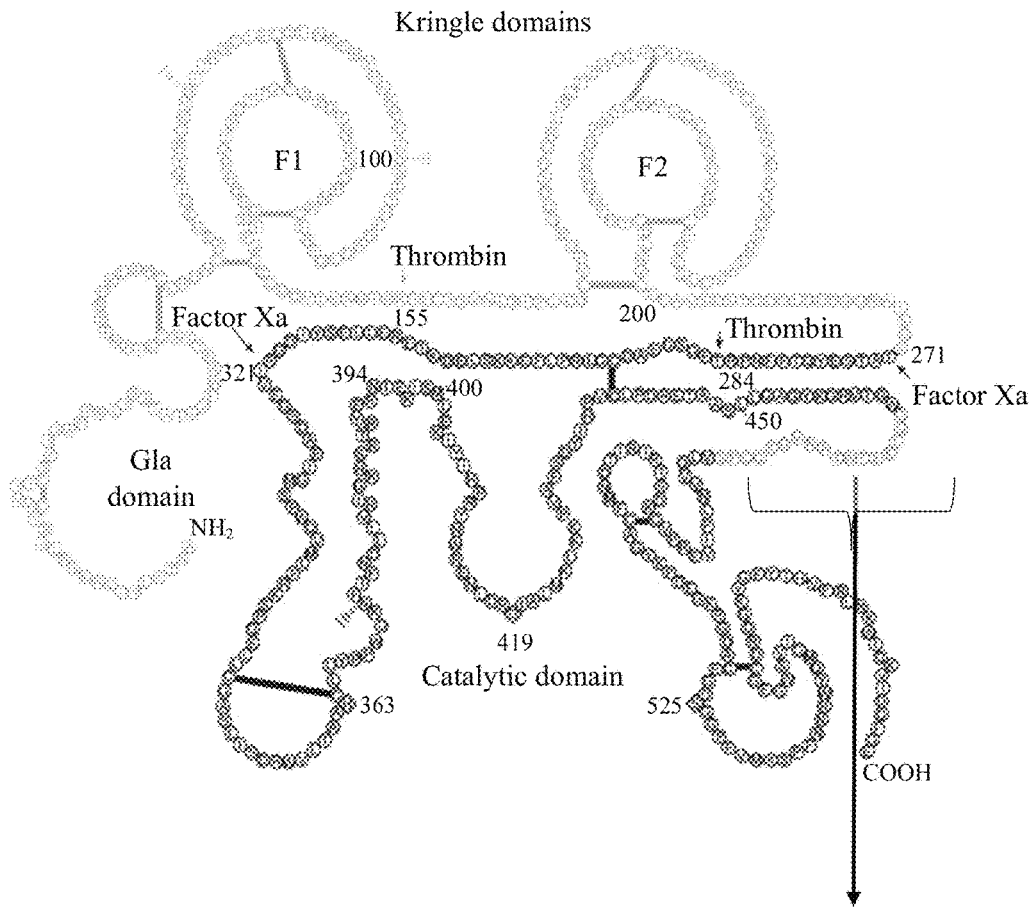
FIG. 1 provides an illustration of the prothrombin molecule. The sequence which is cleaved during prothrombin activation is shown as light gray silhouette. The mature alpha-thrombin sequence is shown in black. The gamma loop peptide sequence is silhouetted in the thrombin primary sequence, and is shown separately below the prothrombin molecule (indicated by an arrow, SEQ ID NO:1). SEQ ID NO:2 is a peptide comprising the gamma loop sequence (marked with brackets) with three and four amino acids flanking on the N- and C-termini, respectively.

The present disclosure is based, in part, upon the finding that compounds, in particular, certain isolated peptides which include the thrombin gamma loop sequence or interact with the thrombin gamma loop are capable of stabilizing thrombin activity in a thrombin liquid formulation.

"Stabilizing thrombin activity" refers to, for example, reducing thrombin autolytic activity.

"Stabilizing thrombin activity" may also refer to maintaining thrombin activity when stored for more than one day, e.g. at room temperature as an aqueous thrombin solution e.g. a concentrated thrombin solution, without significantly compromising thrombin's biological activity towards heterologous substrates, including the activity of conversion of fibrinogen to fibrin.

"Room temperature" is meant to include temperature of about 20° C. to about 28° C., or 22° C. to about 26° C.

The term "stabilizing" means, for example, maintaining the thrombin activity within the thrombin liquid formulation at a level of about 80% to about 100% (e.g. about 90 to 100%) compared to the initial thrombin activity.

The term "initial thrombin activity" refers, for example, to the activity of thrombin towards fibrinogen measured in a thrombin liquid formulation immediately after thawing a frozen thrombin formulation, immediately after reconstituting thrombin powder and/or before storage of liquid thrombin under conditions that allow self degradation (e.g. more than one month storage at 2-8° C.; more than 1 day at room temperature e.g. at concentrations of 10 IU/ml to 5,000 IU/ml thrombin or more) thrombin.

It was found that a linear or cyclic (i.e. intramolecular S—S bonds) gamma loop peptide or linear or cyclic peptide which contains the consecutive amino acid sequence of the thrombin gamma loop; peptides known to interact with the gamma loop of thrombin; and randomly selected peptide that show a binding interaction with the gamma loop stabilize liquid thrombin.

It was found that peptides comprising the gamma loop sequence (SEQ ID NO: 2 and SEQ ID NO:3), whether linear or cyclic, displayed an efficient stabilization of thrombin activity. The cyclic gamma peptide (SEQ ID NO:3) showed only ~7% inhibition of thrombin at 0.5 mM, and the linear gamma peptide (SEQ ID NO:1) exhibited about 20% inhibition It was found that stabilization of thrombin with cyclic peptides mutated in residues E, N or G of the gamma loop was inefficient (SEQ ID NOS: 4, 5, and 6, respectively).

Two random peptides (SEQ ID NOS:12 and 13), selected from a random library on the basis of their initial binding to the gamma loop, yielded stabilization effect of thrombin.

Binding of a molecule e.g. a peptide to the gamma loop, appears to be a good predictor of their stabilizing potential.

Two thrombin derived peptides [Thr 031 CS (SEQ ID NO:9)], Thr 032 CS (SEQ ID NO:10)] which are capable of interacting with the gamma loop peptide, showed stabilization effect on thrombin and exhibited a minor inhibitory effect on thrombin at the same concentrations (e.g. 0.5 mM peptide: 13-14% inhibition).

It was found that peptides with sequence set forth in SEQ ID NOS: 2, 3, 7, 9, 10, 11, 12 and 13 were capable of stabilizing liquid aqueous thrombin.

The stabilized thrombin, comprising the molecules/peptides found according to the invention, can be used directly for activating fibrinogen e.g. without dilution and/or removal of the molecules/peptides.

For stability testing, 1000IU/ml thrombin following storage with or without peptides can be used and activity testing can be carried out as described herein. Dilutions (1:100) can be carried out before measuring the activity.

For inhibition testing, the clotting activity of 10 IU/ml thrombin can be measured in the presence or absence of peptides (without their dilution).

Thrombin activity towards fibrinogen can be assessed by measuring thrombin clotting activity. The clotting activity can be measured directly, for example, by the modified, European Pharmacopeia Assay (0903/1997) procedure and/or indirectly, such as measuring migration length on a slanted surface (or drop test model), or by any other method known in the art.

Provided herein are compounds e.g. isolated peptides that include a thrombin gamma loop sequence or that interact with the thrombin gamma loop. Further provided herein is a method of identifying compounds capable of stabilizing thrombin activity in an aqueous liquid thrombin formulation.

Provided herein are compounds capable of stabilizing the activity of thrombin in a liquid thrombin formulation. The compounds are selected from the group consisting of isolated peptides comprising the amino acid sequence of the thrombin gamma loop, derivatives or salts thereof and thrombin gamma loop interacting molecules, and derivatives or salts thereof.

A peptide comprising the amino acid sequence of the thrombin gamma loop and a thrombin gamma loop interacting molecule are different form the intact alpha thrombin.

Amino Acids

Amino acids and peptide sequences are commonly abbreviated as shown below, in Table A.

TABLE A

Abbreviation, systematic name and formulae of common amino acids

| Name | Symbols/abbreviations 3 ltr | 1 ltr | Systematic name | Formula |
|---|---|---|---|---|
| Alanine | Ala | A | 2-Aminopropanoic acid | CH3—CH(NH2)—COOH |
| Arginine | Arg | R | 2-Amino-5-guanidinopentanoic acid | H2N—C(=NH)—NH—[CH2]3—CH(NH2)—COOH |
| Asparagine | Asn | N | 2-Amino-3-carbamoylpropanoic acid | H2N—CO—CH2—CH(NH2)—COOH |
| Aspartic acid | Asp | D | 2-Aminobutanedioic acid | HOOC—CH2—CH(NH2)—COOH |
| Cysteine | Cys | C | 2-Amino-3-mercaptopropanoic acid | HS—CH2—CH(NH2)—COOH |
| Glutamine | Gln | Q | 2-Amino-4-carbamoylbutanoic acid | H2N—CO—[CH2]2—CH(NH2)—COOH |
| Glutamic acid | Glu | E | 2-Aminopentanedioic acid | HOOC—[CH2]2—CH(NH2)—COOH |
| Glycine | Gly | G | Aminoethanoic acid | CH2(NH2)—COOH |
| Histidine | His | H | 2-Amino-3-(1H-imidazol-4-yl)propanoic acid | NH—CH=N—CH=C—CH2—CH(NH2)—COOH |
| Isoleucine | Ile | I | 2-Amino-3-methylpentanoic | C2H5—CH(CH3)—CH(NH2)—COOH |
| Leucine | Leu | L | 2-Amino-4-methylpentanoic acid | (CH3)2CH—CH2—CH(NH2)—COOH |
| Lysine | Lys | K | 2,6-Diaminohexanoic acid | H2N—[CH2]4—CH(NH2)—COOH |
| Methionine | Met | M | 2-Amino-4-(methylthio)butanoic | CH3—S—[CH2]2—CH(NH2)—COOH |
| Phenylalanine | Phe | F | 2-Amino-3-phenylpropanoic acid | C6H5—CH2—CH(NH2)—COOH |
| Proline | Pro | P | Pyrrolidine-2-carboxylic acid | NH—CH2)3—CH—COOH |
| Serine | Ser | S | 2-Amino-3-hydroxypropanoic acid | HO—CH2—CH(NH2)—COOH |
| Threonine | Thr | T | 2-Amino-3-hydroxybutanoic acid | CH3—CH(OH)—CH(NH2)—COOH |
| Tryptophan | Trp | W | 2-Amino-3-(lH-indol-3-yl)-propanoic acid | Ph—NH—CH=C—CH2—CH(NH2)—COOH |
| Tyrosine | Tyr | Y | 2-Amino-3-(4-hydroxyphenyl)-propanoic acid | HO—p-Ph—CH2—CH(NH2)—COOH |
| Valine | Val | V | 2-Amino-3-methylbutanoic acid | (CH3)2CH—CH(NH2)—COOH |

In one embodiment, an amino acid analog sequence is used whereby at least one amino acid in the isolated peptide is substituted with an analog or bio-similar amino-acid (conservative substitution), as known in the art.

The amino acids can be in L-form, D-form, or their derivatives (e.g. pseudo amino acid, functionalized amino acid (e.g. fluorinated amino acid . . . etc.), beta amino acid, gamma amino acid . . . etc.).

Thrombin

Thrombin is a serine protease which results from the cleavage of prothrombin (Factor II), a zymogen, by another serine protease (Factor Xa). Human thrombin is a 295 amino acid protein composed of two polypeptide chains joined by a The zymogen prothrombin (shown in FIG. 1) is cleaved at residue 271, removing the entire N-terminal 271 amino acids. An additional intramolecular cleavage by Factor Xa at residue 320 yields the active alpha thrombin molecule which is a 295 amino acid polypeptide (human) composed of a heavy and light chain held together via a single S-S bond (Krishnaswamy J, (2013) "The transition of prothrombin to thrombin". J Thromb Haemost. Jun;11 Suppl 1:265-76.) Thrombin, being a serine protease, can initiate its own degradation ("autolysis") by cleaving other thrombin molecules at the beta (residue 382 and 394) or gamma (residue 443 and residue 474) sites, yielding beta- and gamma-thrombin, respectively.

Neither of these loops contain a classic thrombin recognition site, nor is this cleavage specific to a certain residue within the loops. Rather, these loops are both flexible and exposed and are cleaved for lack of a proper substrate and especially at high thrombin concentration (see for example, Chang, J Y. Biochem. J. (1986) 240:797-802, "The structures and proteolytic specificities of autolysed human thrombin"; Rydel T J, et al., J Biol Chem. 1994, 269(35):22000-6.Crystallographic structure of human gamma-thrombin"; Pozzi N, et al., Biophys Chem. 2011, 159(1):6-13 "Rigidification of the autolysis loop enhances Na(+) binding to thrombin"). The inactivation of thrombin in-vivo does not proceed via this mechanism (autolysis) but rather via a specific interaction (bridged by heparin) with the serine protease inhibitor (SERPIN), anti-thrombin III (ATIII).

The interaction of thrombin (and several other homologous serine proteases such as Factor X and even protein C) with ATIII is mediated via the gamma loop (see, for example, Yang, L., Blood. 2004, 104(6):1753-9, "Heparin-activated antithrombin interacts with the autolysis loop of target coagulation proteases"; and Marino, F, J Biol Chem. 2010, 285(25):19145-52. "Engineering thrombin for selective specificity toward protein C and PAR1").

Human and non-human thrombin can be used within the present invention. Thrombin is used medically e.g. as a hemostatic agent and as a component of tissue adhesive.

In one aspect, provided herein is a thrombin formulation comprising: a) thrombin; and b) a compound capable of stabilizing thrombin activity, the compound selected from the group consisting of: an isolated peptide comprising the amino acid sequence of the thrombin gamma loop, a derivative or salt thereof; and a thrombin gamma loop interacting molecule, a derivative or salt thereof; and a pharmacologically acceptable excipient.

For long-term storage, the formulation, comprising the thrombin and the compound, is aliquoted into sterile vials, ampoules, or other containers, which are then sealed. In one embodiment, a seal that permits removal of the stabilized thrombin composition with a syringe through the seal is used. The container can be labeled according to standard practice in the pharmaceutical or medical device field.

In one embodiment of the invention, the container is provided in a kit with a second container containing a scaffold, such a gelatin or collagen based matrix. In another embodiment, the container is provided in a kit with a second container comprising a fibrinogen comprising component. The kit may further comprise an application device, such as a sprayer, syringe, or the like and/or a diluent and/or instructions for use.

In use, the stabilized thrombin formulation can be used directly from the container or can be further diluted to the desired concentration, generally the thrombin activity in the formulation is from about 1 IU/ml to about 10,000 IU/ml, typically about 10 IU/ml to 5,000 IU/ml, or 10 IU/ml to 1,000 IU/ml although the actual concentration will be determined by the user (e.g. physician, nurse, medic) i.e. according to the needs of the individual patient and on the severity of bleeding. The stabilized thrombin can be applied to bleeding tissue to achieve hemostasis, per se or may be used in combination with a scaffold or matrix, for example, an absorbable scaffold or matrix. The stabilized thrombin formulation can also be used as a component of a tissue adhesive, fibrin sealant or fibrin glue. These and other known in the art uses of thrombin are contemplated for the disclosed stabilized thrombin. Numerous uses of fibrin glue in various fields have been reported, including use as a sealant e.g. for sealing leaks, hemostatic agent/stop bleeding, adhesion prevention, to enhance healing, for joining structures, in a variety of open and laparoscopic surgeries.

Preferred hemostatic scaffolds are natural or genetically engineered absorbable polymers or synthetic absorbable polymers, or mixtures thereof. Examples of natural or genetically engineered absorbable polymers are proteins, polysaccharides and combinations thereof. Proteins include, prothrombin, thrombin, fibrinogen, fibrin, fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, collagen, elastin, albumin, gelatin, platelet surface glycoproteins, vasopressin, vasopressin analogs, epinephrine, selectin, procoagulant venom, plasminogen activator inhibitor, platelet activating agents, synthetic peptides having hemostatic activity, and/or combinations thereof. Polysaccharides include, without limitation, cellulose, alkyl cellulose, e.g. methylcellulose, alkylhydroxyalkyl cellulose, hydroxyalkyl cellulose, cellulose sulfate, salts of carboxymethyl cellulose, carboxymethyl cellulose, carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, heparin, heparin sulfate, heparan, heparan sulfate, dermatan sulfate, keratan sulfate, carrageenans, chitosan, starch, amylose, amylopectin, polyN-glucosamine, polymannuronic acid, polyglucuronic acid, and derivatives of any of the above. Examples of synthetic absorbable polymers are aliphatic polyester polymers, copolymers, and/or combinations thereof.

The prothrombin/thrombin molecule and the gamma loop chain sequence are illustrated in FIG. 1.

Definitions

As used herein, the indefinite articles "a" and "an" mean "at least one" or "one or more" unless the context clearly dictates otherwise.

As used herein, the terms "comprising", "including", "having" and grammatical variants thereof are to be taken as specifying the stated features, steps or components but do not preclude the addition of one or more additional features, steps, components or groups thereof.

When a numerical value is preceded by the term "about", the term "about" is intended to indicate +/−10%.

As used herein, the term "peptide" is used broadly to mean an isolated compound of about 5 to about 100 consecutive amino acids, or analogs of amino acids. Included within the definition of peptide are, for example, peptides containing one or more analogs of an amino acid (including, for example, unnatural amino acids, peptoids, etc.), peptides with substituted linkages, as well as other modifications known in the art, both naturally occurring and non-naturally occurring (e.g. synthetic). Thus, synthetic peptides, cyclized, branched peptides and the like, are included within the definition. Non-limiting lengths of peptides suitable for use in the present invention includes peptides of 5 to 100 residues (amino acids and/or analogs) in length (or any integer therebetween), 5 to 20 residues in length, 6 to 75 residues in length, 10 to 25 residues in length, 21 to 75 residues in length, 75 to 100 residues in length. Typically, peptides useful in this invention can have a maximum length suitable for the intended application. Preferably, the peptide is between about 5 and 30 residues in length e.g. between about 5 and 30 consecutive amino acid residues; for example, about 5, 6, 7, 8, 9, 10, 11, 12, 13, 14, 15, 16, 17, 18, 19, 20, 21, 22, 23, 24, 25, 26, 27, 28, 29, or 30 consecutive amino acid residues, preferably about 10 to 17 or 10 to 15 residues in length.

Furthermore, a peptide as described herein, for example synthetic peptides, may include additional molecules such as labels or tracers, linkers, or other chemical moieties (e.g. biotin, dyes) covalently attached thereto or non-covalently associated therewith. Such moieties may further enhance interaction of the peptides with the compound e.g. thrombin gamma loop peptide and/or aid in detection or quantification of stabilized thrombin.

The term peptides also includes derivatives of the amino acid sequences of the invention having one or more substitution, addition and/or deletion, including one or more non-naturally occurring amino acid. Preferably, derivatives exhibit at least about 50% identity to any wild type or reference sequence, preferably at least about 70% identity, more preferably at least about 75%, 80%, 85%, 90%, 91%, 92%, 93%, 94%, 95%, 96%, 97%, 98%, 99% or 100% sequence identity to any wild type or reference sequence described herein. Peptide derivatives can include modifications to the native sequence, such as deletions, additions and substitutions (generally conservative in nature), so long as the peptide maintains the desired activity e.g. stabilization of thrombin. These modifications may be deliberate, as through site-directed mutagenesis, or may be accidental, such as through synthesis or mutations of hosts that produce the proteins or errors due to PCR amplification. Further encompassed herein are pharmaceutically acceptable salts of peptides and the derivatives of such salts.

By "gamma loop peptide" is meant a peptide of ten (10) consecutive amino acid sequence set forth in SEQ ID NO:1, specifically the sequence KETWTANVGK (LYS-GLU-THR-TRP-THR-ALA-ASN-VAL-GLY-LYS). Without wishing to be bound to theory, the sequence of the thrombin gamma loop is homologous to and corresponding to residues 145-150 in bovine chymotrypsin according to the classic numbering system of this protein family and has been shown using X-ray crystallography to maintain a general exposed loop structure. Sequences homologous to the thrombin gamma loop can be contemplated as derivatives of the thrombin gamma loop.

"Thrombin" or "thrombin polypeptide" is a mammalian serine protease which is part of the blood coagulation cascade and converts fibrinogen into insoluble strands of fibrin, as well as catalyzes other coagulation-related reactions. In humans, prothrombin is encoded by the F2 gene, and the resulting polypeptide is proteolytically cleaved in the coagulation cascade to form thrombin. Thrombin serves, inter alia, as an active component in several hemostasis products. For example, fibrin sealants typically comprise a fibrinogen component and a thrombin component. When both components are mixed (e.g. when applied to a bleeding wound) thrombin cleaves fibrinogen and a fibrin polymer is formed.

One skilled in the art will recognize that the peptides disclosed herein may be synthesized as derivatives of the peptides, including "peptide mimetics". A peptide mimetic or "peptidomimetic", is a molecule that is not completely peptidic in nature, yet mimics the biological activity of the peptide upon which it is structurally based. Such peptidomimetics include peptide-like molecules containing non-naturally occurring amino acids. A peptidomimetic can include one or more amino acid analogs and can be a peptide-like molecule which contains, for example, an amide bond isostere such as a retro-inverso modification; reduced amide bond; methylenethioether or methylenesulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. The terms also include molecules comprising one or more N-substituted glycine residues (a "peptoid") and other synthetic amino acids or peptides. (See, e.g., U.S. Pat. Nos. 5,831,005; 5,877,278; and 5,977,301; Nguyen et al. (2000) Chem Biol. 7(7):463-473; and Simon et al. (1992) Proc. Natl. Acad. Sci. USA 89(20):9367-9371 for descriptions of peptoids). One skilled in the art understands that these and other peptidomimetics are encompassed within the meaning of the term "peptidomimetic" as used herein.

The amino acid sequence of a peptide is written according to the conventional notation, with an amino group (NH2) at the N-terminal appearing on the left hand of the sequence and carboxyl group (COOH) at the C-terminal appearing on the right hand thereof.

The peptides disclosed herein may form a physiologically acceptable salt by conventional salt formation reaction. Such salts can include salts with inorganic acids such as hydrochloric acid, sulfuric acid and phosphoric acid; salts with organic acids such as lactic acid, tartaric acid, maleic acid, fumaric acid, oxalic acid, malic acid, citric acid, oleic acid and palmitic acid; salts with hydroxides and carbonates of alkali metals and alkali earth metals such as sodium, potassium, calcium and aluminum; and salts with amines such as triethylamine, benzylamine, diethanolamine, t-butylamine, dicyclohexylamine and arginine.

Both inter- and intra-chain disulfide bonds may be formed and the peptide formed resulting from the formation of such disulfide bonds are encompassed by the present invention.

In one embodiment, the peptides disclosed herein are chemically synthesized. In other embodiments, the peptides disclosed herein are produced in-vivo or ex-vivo by expression of recombinant DNA in prokaryotic or eukaryotic host cells.

In other embodiments, the peptides disclosed herein are produced in-vivo or ex-vivo by expression of a vector comprising the nucleic acid sequence encoding the compound disclosed herein in prokaryotic or eukaryotic host cells.

The terms "isolated polynucleotide", "isolated nucleic acid sequence" and "an isolated nucleic acid molecule" are used herein interchangeably. An isolated "polynucleotide" can include both double- and single-stranded sequences and refers to, but is not limited to, prokaryotic sequences, eukaryotic mRNA, cDNA from viral, prokaryotic or eukaryotic mRNA, genomic RNA and DNA sequences from viral (e.g. RNA and DNA viruses and retroviruses), prokaryotic DNA or eukaryotic (e.g. mammalian) DNA, and synthetic DNA sequences. The term also encompasses sequences that include known base analogs of DNA and RNA, and includes modifications such as deletions, additions and substitutions (generally conservative in nature), to the native sequence. Modifications of polynucleotides may have any number of effects including, for example, facilitating expression of the peptide in a host cell. Typically, the polynucleotide encodes peptides of at least 5, 6, 7, 8, 9, 10, 11, 12, 13, 14, 15, 16, 17, 18, 19, 20, 21, 22, 23, 24, 25, 30 or even more amino acids.

A "polynucleotide coding sequence" or a sequence that "encodes" a selected polypeptide, is a nucleic acid molecule that is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxyl) terminus. A transcription termination sequence may be located 3' to the coding sequence. Typical "control elements," include, but are not limited to, transcription regulators, such as promoters, transcription enhancer elements, transcription termination signals, and polyadenylation sequences; and translation regulators, such as sequences for optimization of initiation of translation, e.g. Shine-Dalgarno (ribosome binding site) sequences, Kozak sequences (i.e., sequences for the optimization of translation, located, for example, 5' to the coding sequence), leader sequences (heterologous or native), translation initiation codon (e.g. ATG), and translation termination sequences. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is included by an analyte, cofactor, regulatory protein, etc.), and constitutive promoters.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

A "recombinant" nucleic acid molecule as used herein to describe a nucleic acid molecule means a polynucleotide of genomic, cDNA, semi synthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting prokaryotic microorganisms or eukaryotic cell lines cultured as unicellular entities, are used interchangeably, and refer to cells which can be, or have been, used as recipients for constructs, vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

By "isolated" is meant, when referring to a polynucleotide or a peptide, that the indicated molecule or compound is separate and discrete from the whole organism with which the molecule or compound is found in nature or, when the polynucleotide or peptide is not found in nature, is sufficiently free of other biological macromolecules so that the polynucleotide or peptide can be used for its intended purpose.

As used herein, a molecule e.g. a peptide is said to "interact" with or "bind" to another peptide or protein (e.g. a thrombin gamma loop interacting molecule with thrombin) if it associates with the peptide or protein via non-covalent binding forces, for example van der Waals and electrostatic forces. A molecule e.g. a peptide is said to "interact preferentially" with a particular domain in a protein (e.g. the thrombin gamma loop) if it associates with greater affinity and/or greater specificity to the particular domain than to another domain in the protein. In some embodiments, the molecule e.g. peptide binds preferentially to the gamma loop of thrombin. It is to be understood that a preferential interaction does not necessarily require interaction between specific amino acid residues and/or motifs of each peptide.

"Thrombin activity" and "thrombin biological activity" is meant to include thrombin mediated conversion of heterologous substrates, including proteins e.g. fibrinogen into fibrin, as well as the conversion of Factor VIII to Factor VIIIa, XI to XIa, XIII to XIIIa, and Factor V to Va. A "heterologous substrate" is a substrate, preferably a protein substrate, other than thrombin. In some embodiments, the thrombin activity refers to conversion of fibrinogen into fibrin. The term "without significantly compromising thrombin's (biological) activity" refers to retaining thrombin activity towards fibrinogen at a level of at least 60%, at least 70% and preferably at least 80%, or at least 90% or more e.g. 91%, 92%, 93%, 94%, 95%, 96%, 97%, 98%, 99% compared to uninhibited/unstabilized thrombin and/or compared to the initial thrombin activity.

As used herein the terms "autolysis" or "auto degradation" refer to the unfavorable molecular degradation of thrombin into an inactive or partially active form.

A preferred compound as disclosed herein, is a compound capable of stabilizing thrombin activity, for example, by reducing thrombin autolysis without significantly compromising thrombin activity e.g. towards fibrinogen.

In one embodiment, the stabilized aqueous liquid thrombin formulation is stable for more than one month storage at a temperature of 2 to 8° C.; for 72 hours at 37° C.; and/or for 144 hours at 37° C.

In some embodiments the compound inhibits autolysis of thrombin by about 60% to about 100% or about 60% to about 95%, preferably by about 70% to about 90%, and retains about 60% to about 100% or about 60% to about 95%, about 70% to about 90%, preferably about 80% to about 95% thrombin biological activity, e.g. after one month storage at a temperature of 2 to 8° C. in liquid form; after 72 hours at about 37° C.; after 144 hours at about 37° C.

The term "affinity" refers to the strength of binding and can be expressed quantitatively as a dissociation constant ($K_d$). A molecule e.g. a peptide disclosed herein can interact with the gamma loop of thrombin with at least 2 fold greater affinity, more preferably at least 5 fold greater affinity and even more preferably at least 10, 20, 30, 40 or 50-fold greater affinity than it interacts with another domain of thrombin. Binding affinity (i.e., $K_d$) can be determined using standard techniques.

The term "an effective amount" refers to the amount of a compound disclosed herein required to stabilize thrombin while substantially retaining thrombin activity e.g. towards fibrinogen (e.g. conversion of fibrinogen to fibrin). The effective amount of a compound used to practice the present invention for stabilization of thrombin may vary depending upon the concentration of thrombin in a composition/formulation. Such amount is referred to as an "effective amount".

The "pharmaceutically acceptable" or "pharmacologically acceptable" carriers, solvents, diluents, excipients, and vehicles generally refer to inert, non-toxic solid or liquid fillers, diluents or encapsulating material not reacting with the active ingredients of the compositions disclosed herein. Acceptable excipients include, without limitation, saline; acetic acid or acetate; calcium, sodium and chloride ions; mannitol; albumin; or combination thereof.

The term "contacting" is used herein in its broadest sense and refers to any type of combining action. Contacting includes, but is not limited to, mixing, admixing and/or adding.

Peptide Synthesis

Peptides disclosed herein may be synthesized according to methods known in the art, including, but not limited to synthetic (e.g. synthesizing the peptide chemically from individual amino acids) and recombinant methods (e.g. synthesizing DNA encoding the peptide and using the DNA to produce recombinant peptide).

Chemical synthesis of the peptide: a peptide disclosed herein and DNA encoding the peptide may be chemically synthesized by methods known in the art. Suitable methods for synthesizing the peptide are described by Stuart and Young (1984), "Solid Phase Peptide Synthesis", Solid Phase Peptide Synthesis, Methods Enzymol., Second Edition, Pierce Chemical Company, 289, Academic Press, Inc., NY (1997). For example, a solid phase synthesis method or a liquid phase synthesis method may be used. The solid phase synthesis is usually carried out by protecting amino groups with appropriate protecting groups. For example, either Boc (tert-butoxycarbonyl) or Fmoc (9-fluorenylmethyloxycarbonyl), or a combination thereof may be used. In one example, a peptide disclosed herein is synthesized by following the steps: 1) an amino acid residue corresponding to the C-terminal of the peptide to be produced is bonded to a solid phase material insoluble to a reaction solvent via an a-COOH group of the amino acid or such solid phase material is purchased; 2) in the direction towards the N-terminal of the peptide, a corresponding amino acid or peptide fragment is bonded by condensation to the amino acid of step 1) after protecting other functional groups such as an a-amino group of the corresponding amino acid or peptide fragment other than an a-COOH group; 3) a protecting group of an amino group forming a peptide bond such as an a-amino group is removed from the bonded amino acid or peptide fragment; 4) steps 2) and 3) are repeated to elongate a peptide chain in order to form a peptide chain corresponding to the desired peptide; 5) detach the produced peptide chain from the solid phase material and remove the protecting groups from the protected functional groups; and 6) purify the peptide, thereby to obtain the desired peptide.

Solid phase materials, as well as solvents and a condensing agents, are well known in the art.

Chemical synthesis and expression of DNA: The DNA encoding a peptide disclosed herein may be replicated and used to express recombinant peptide following insertion into a wide variety of host cells in a wide variety of cloning and expression vectors. The host may be prokaryotic or eukaryotic. The DNA may be chemically synthesized. Suitable methods for synthesizing DNA and cloning vectors (e.g. for use in mammalian, insect or plant cells, bacteria, phage and yeast) are available. The recombinant peptide, which can be expressed in the form of a fusion protein, is purified by methods known in the art.

Compounds Useful in Practicing the Present Invention

Provided herein are compounds and methods for stabilization of thrombin activity in liquid thrombin formulation, wherein stabilizing the thrombin activity refers, for example, to reducing or preventing autolytic activity without significantly compromising the thrombin's biological activity. The compounds are selected from the group consisting of an isolated peptide comprising the amino acid sequence of the thrombin gamma loop peptide, a derivative or salt thereof; or a thrombin gamma loop interacting molecule which may be an isolated interacting peptide, an isolated antibody or antibody fragment thereof, a nucleotide aptamer and a peptide aptamer, a derivative or a salt of such a molecule.

Molecules that interact with the gamma loop of thrombin may be identified in a screen and may be tested for their ability to stabilize thrombin activity, using, for example, the methods disclosed herein. In some embodiments, the interacting molecule is an isolated peptide, a peptidomimetic of such peptide, or a salt of such peptides. Examples of interacting peptides are provided herein, for example in SEQ ID NOS: 7, and 9-13.

Peptides may be linear, branched or cyclized. For example, peptides represented by SEQ ID NO:1 and 2 are linear, and the peptide represented by SEQ ID NO:3 is cyclic.

In some embodiments, the interacting molecule is an isolated antibody, a fragment of such antibody, or a salt of such antibody. The term "antibody" refers to IgG, IgM, IgD, IgA, and IgE antibody, inter alia, and includes polyclonal antibodies and monoclonal antibodies. In one embodiment the antibody is directed towards, was raised against, and/or recognizes the thrombin gamma loop. This term refers to whole antibodies or fragments of antibodies comprising an antigen-binding domain, e.g. antibodies without the Fc portion, single chain antibodies, miniantibodies, fragments consisting of essentially only the variable, antigen-binding domain of the antibody, etc. The term also encompasses antibody derivatives such as antibody fragments which retain the ability to selectively bind with their antigen or receptor and are exemplified as follows, inter alia:

(1) Fab, the fragment which contains a monovalent antigen-binding fragment of an antibody molecule which can be produced by digestion of whole antibody with the enzyme papain to yield a light chain and a portion of the heavy chain;

(2) (Fab')$_2$ of the antibody is a dimer of two Fab fragments held together by disulfide bonds, that can be obtained by treating whole antibody with the enzyme pepsin without subsequent reduction.

(3) Fv, defined as a genetically engineered fragment containing the variable region of the light chain and the variable region of the heavy chain expressed as two chains; and (4) Single chain antibody (SCA), defined as a genetically engineered molecule containing the variable region of the light chain and the variable region of the heavy chain linked by a suitable polypeptide linker as a genetically fused single chain molecule.

In some embodiments, the interacting molecule is an aptamer or a salt of such aptamer. Aptamers are RNA and/or DNA single-strand or double-strand oligonucleotides, which bind to a target protein and do not generally exhibit non-specific effects. Aptamers can be modified for stability or other desired qualities in accordance with any nucleic acid modifications known to one of skill in the art. Modifications to an aptamer can be introduced anywhere in the molecule, such as the 5' or 3' termini, or at any internally defined modification site. Thioaptamers are aptamers which contain sulfur modifications at specific internucleoside phosphoryl sites, and may possess enhanced stability, nuclease resistance, target affinity and/or selectivity. Examples of thioaptamers include phosphoromonothioate (S-ODN) and phosphorodithioate (S2-ODN) oligodeoxy thioaptamers. Further information on aptamers and thioaptamers can be found in U.S. Pat. Nos. 5,218,088 and 6,423,493.

Details of the exemplary compounds useful in practicing the invention, are provided in the Examples, hereinbelow and in the sequence listing, incorporated herewith.

Methods of Screening

Provided herein are methods of screening for compounds capable of stabilizing thrombin activity. Accordingly, provided is a method for screening for a compound capable of stabilizing the activity of thrombin in a liquid thrombin formulation, comprising:

a) providing an isolated peptide comprising the amino acid sequence of the thrombin gamma loop;

b) providing a set of test compounds;

c) contacting the isolated peptide of (a) with the set of test compounds of (b); and d) identifying one or more compounds, which bind to the peptide;

whereby the binding indicates a potential use of the compound in stabilizing thrombin activity.

In some embodiments, the method further includes the step of isolating the one or more compounds identified in step d) and/or of testing the one or more compounds identified in step d) for its ability to stabilize thrombin activity.

While the following examples demonstrate certain embodiments of the invention, they are not to be interpreted as limiting the scope of the invention, but rather as contributing to a complete description of the invention.

EXAMPLES

Example 1

Thrombin Activity Assay

Aqueous liquid thrombin, in its purified and concentrated form 1000 international units IU/ml may undergo autolysis at room temperature causing a significant loss of activity e.g. towards a heterologous substrate. E.g. thrombin activity towards a heterologous substrate is reduced when a liquid thrombin formulation is incubated at room temperature for prolonged periods of time (e.g. 72 to 144 hours), inter alia, due to autolytic degradation. The decrease of thrombin activity towards a heterologous substrate in aqueous liquid solution can be assessed by measuring thrombin activity after prolonged periods of time and under permissive temperature (e.g. 37° C.). In the following experiments, the effect of a peptide on the stability of thrombin was studied under different conditions.

Aqueous liquid purified and concentrated thrombin (1000 IU/ml; equivalent to about 10 μM) was aliquoted and placed in a 37° C. incubator for 3 days (72 hours), 7 days (168 hours) and 14 days (336 hours). Prior to incubation, thrombin samples were spiked with indicated amounts of different tested peptides or with a control thrombin inhibitor: benzamidine or arginine *HCl ("arginine"). Specific peptides, their concentrations, and thrombin inhibitors used are indicated in each Example. Following the incubation period, the samples were frozen at −80° C. until testing the thrombin activity. Just before thrombin activity assay testing, all the samples were thawed and 100-fold diluted into a dilution buffer (0.4% tri-sodium citrate di-hydrate, 0.9% sodium chloride and 1% BSA, pH=7.5) to bring the thrombin concentration in the sample to that within the specifications of the assay (4-10 IU/ml) and to dilute the tested peptides in the sample to a negligible concentration.

Thrombin activity was assessed by clotting time measurements using STart4 Coagulation Instrument (DIAGNOSTICA STAGO™, Asnieres sur Seine, France). The assay is a modification of the European Pharmacopoeia Assay procedure, 1997, 0903, p. 858. Briefly, a calibration curve was prepared by mixing thrombin standard with a fibrinogen solution of 0.1% fibrinogen content (Enzyme Research Laboratories, Ind., USA). Thrombin concentration in the different tested samples was then calculated from the calibration curve by their clotting time (the concentration was extrapolated from the calibration curve).

For stability testing of 1000IU/ml thrombin following storage with or without peptides, testing was carried out as described above. Dilutions (1:100) were carried out before measuring the activity.

For inhibition testing, the clotting activity of 10 IU/ml thrombin was measured in the presence or absence of peptides.

Example 2

The Effect of Peptides Comprising the Amino Acid Sequence of the Thrombin Gamma Loop on Thrombin Stabilization The prothrombin sequence which is cleaved during thrombin formation is shown as light gray silhouette in FIG. 1. The mature alpha-thrombin polypeptide sequence is shown in black. The peptide sequence utilized herein is silhouetted in the thrombin primary sequence, and shown separately below the molecule (indicated by the arrow). The gamma loop peptide sequence is shown (SEQ ID NO:1), per se, and bracketed within a longer peptide which includes amino acids flanking on both N- and C-termini (SEQ ID NO:2; GNLKETWTANVGKGQPS; GLY-ASN-LEU-LYS-GLU-THR-TRP-THR-ALA-ASN-VAL-GLY-LYS-GLY-GLN-PRO-SER). SEQ ID NO:1 was cyclized by synthesizing the peptide with terminal cysteine residues (SEQ ID NO:3; CKETWTANVGKC; CYS-LYS-GLU-THR-TRP-THR-ALA-ASN-VAL-GLY-LYS-CYS). These peptides were synthesized by standard methods.

Figure 2A:
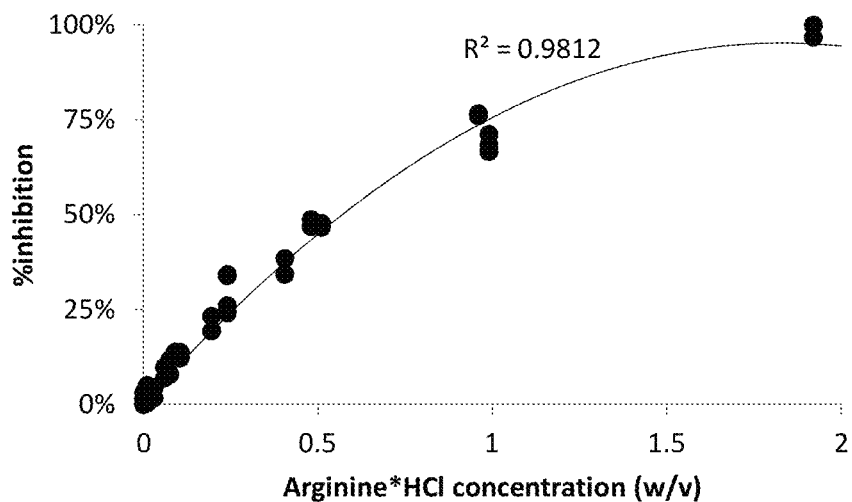
FIG. 2A shows the inhibitory effect that arginine*HCl ("arginine") has on thrombin. Arginine addition to liquid thrombin results in a 50% reduction in thrombin activity at 0.5% (w/v) and >95% reduction in thrombin activity at 2% (w/v).
Figure 2B:
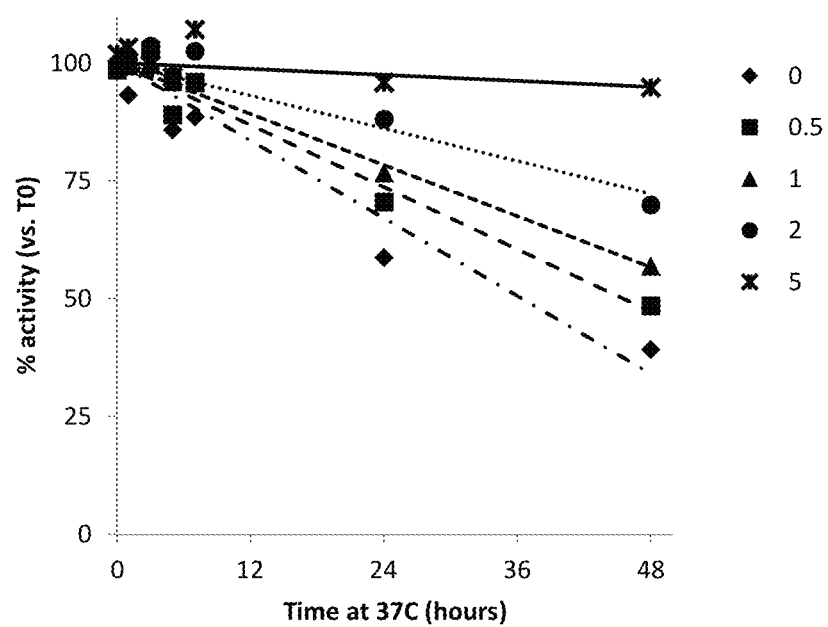
FIG. 2B shows the stabilization level of concentrated thrombin obtained with different concentrations of arginine at 37° C.

The gamma loop peptide with the flanking amino acids (SEQ ID NO:2), and cyclic peptide (SEQ ID NO:3) were used to test for inhibition of thrombin autolytic activity. Arginine *HCl ("arginine"), a thrombin known active site inhibitor, was used as a control. FIG. 2A shows the inhibitory effect that arginine has on thrombin activity (measured using 10 IU/ml thrombin) at different arginine concentrations. FIG. 2B shows the measured % of thrombin after incubation for up to 48 hours at 37° C. with different concentrations of arginine (as shown in the graph). Concentrated thrombin was used for shorter times (up to 48 hours) in order to rapidly obtain a working range for arginine. Arginine displays a dose-dependent effect on thrombin stability correlating to its inhibitory effect seen in FIG. 2A.

Figure 2C:
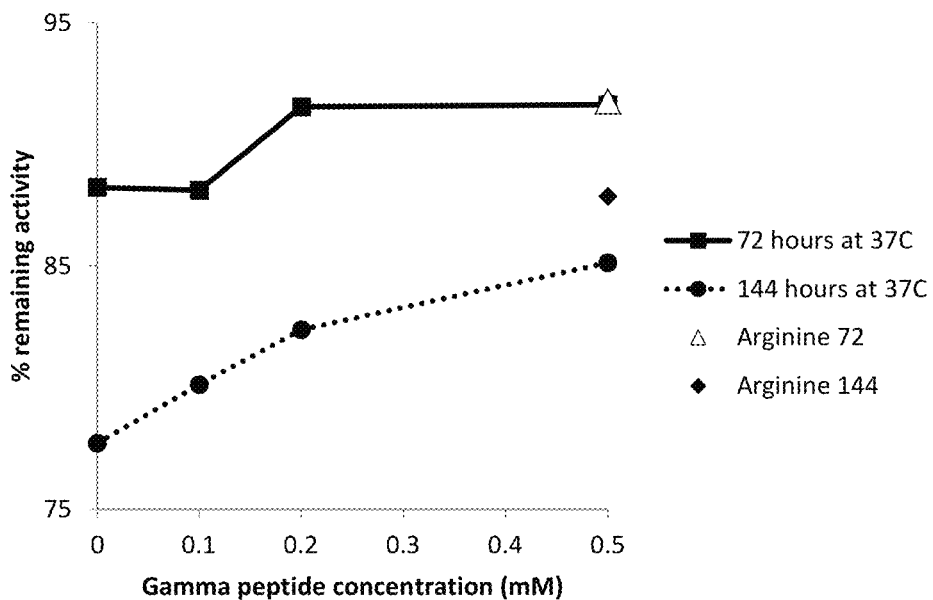
FIG. 2C shows an increase in thrombin stabilization level (% activity remaining over time) obtained by either addition of increasing amounts of a gamma loop peptide to liquid thrombin (1000 IU/ml) or addition of a constant (3% w/v) arginine concentration to liquid thrombin (1000 IU/ml) or without any addition of peptide or inhibitor. Measured was the remaining activity of 1000 IU/ml thrombin after 72 and 144 hours at 37° C.

FIG. 2C shows thrombin remaining activity after incubation with either increasing amounts of gamma loop peptide (SEQ ID NO:2) or with a constant concentration of (3% w/v) arginine. The assay was based on measuring the remaining activity of 1000 IU/ml thrombin after 72 and 144 hours at 37° C.

Figure 2D:
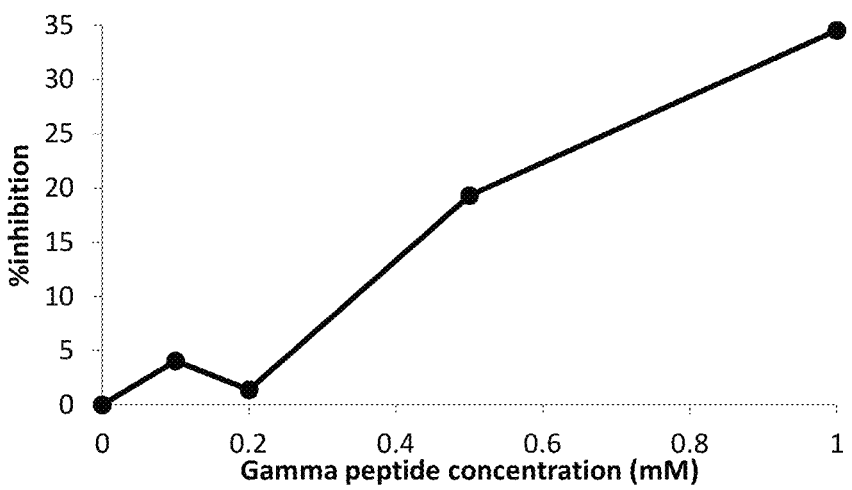
FIG. 2D shows % inhibition of thrombin activity (measured at 10 IU/ml thrombin) by increasing concentration of the gamma peptide.

At 0.1 mM of peptide there was already stabilization detected after 144 hours, and at 0.2 mM it was already evident after 72 hours. FIG. 2D shows inhibition of thrombin activity (measured at 10 IU/ml thrombin) with increasing concentration of peptide. At peptide concentration of 0.2 mM, thrombin activity is not significantly affected Results: A range of 0.5-5% (w/v) arginine maintained thrombin activity following storage (FIG. 2B). However, the presence of arginine compromised thrombin biological activity (see FIG. 2A). Even at 0.5% (w/v) arginine, about 50% (w/v) of the thrombin activity was inhibited and >95% of thrombin activity is inhibited at a concentration of 2% (w/v) (as assayed by its ability to cleave fibrinogen; FIG. 2A). Based on the effective arginine concentration, 3% (w/v) arginine was compared to a 0.5 mM concentration of the gamma loop peptide (SEQ ID NO:2; FIG. 2C). Surprisingly, when the peptide was used at the stabilizing concentration of 0.5 mM, thrombin activity remained high (about 80% remaining activity, see FIG. 2D). In this same experiment, 3% (w/v) arginine was not more effective at maintaining thrombin activity at 72 hours, and only marginally so at 144 hours. This is significant as 3% (w/v) arginine concentration can be extrapolated (based on FIG. 2A) to inhibit thrombin almost entirely.

At a 0.5 mM concentration of peptide, an increase in thrombin stability was observed (FIG. 2C) with a concomitant reduction of thrombin activity towards fibrinogen of only 20% (FIG. 2D). Without wishing to be bound to theory, the gamma loop peptide appears to be, at least partially, an allosteric inhibitor of thrombin degradation.

Example 3

Screening for Mutant Gamma Loop Peptides

A screen was carried out to identify gamma loop mutants that may show improved binding to thrombin. This was carried out with fluorescent thrombin on an array of gamma loop peptide mutants. Three such cyclized peptides with the highest binding efficiency were tested for their capacity to stabilize thrombin without compromising thrombin activity towards fibrinogen (see Example 4 below).

"Gamma loop" (SEQ ID NO:1) shows the wild type sequence of the thrombin gamma loop; E03N refers to the substitution of a asparagine in place of a glutamic acid in position 3 (in SEQ ID NO:4); N08Y refers to the substitution of a tyrosine in place of asparagine in position 8 (in SEQ ID NO:5); G10L refers to the substitution of a leucine in place of a glycine in position 10 (in SEQ ID NO:6).

The amino acid sequences of the peptides are shown in Table 1 herein below:

bodies and kinases with peptide microarrays using radioactive and fluorescence-based assays. Mol Divers 8:291-299.2.). Each peptide was printed in triplicates onto the microarray. For binding studies, 100 μg of purified thrombin (Omrix biopharmaceuticals) were directly labeled with DYLIGHT® 650 Microscale Antibody Labeling Kits, THERMO SCIENTIFIC™ (#84536) and diluted in blocking buffer SUPERBLOKTM T20 (TBS) Blocking Buffer, THERMO SCIENTIFICTM (#37536). The microarrays were incubated with 10 μg/ml DYLIGHT® 650-Thrombin or a Fluorescein-labeled cyclic gamma-loop derived peptide for one hour at 30° C. in a HS4800™ microarray processing station (Tecan) (Masch A, et al., (2010) Antibody signatures defined by high-content peptide microarray analysis. Methods Mol Biol 669:161-172).

Microarrays were washed with 0.1% TWEEN®20 in 1× TBS followed by 0.05% TWEEN®20 in 0.1× SSC and dried in a stream of nitrogen. Each microarray was scanned using GENEPIX® Autoloader 4200AL (Molecular Devices, Pixel

TABLE 1

Mutant gamma loop peptides

| Peptide name | SEQ ID NO: | Peptide SEQ 1-letter | Peptide SEQ 3-letter |
|---|---|---|---|
| Gamma loop | 1 | KETWTANVGK | LYS-GLU-THR-TRP-THR-ALA-ASN-VAL-GLY-LYS |
| AL-cyc_E03N | 4 | CKNTWTANVGKC | CYS-LYS-ASN-THR-TRP-THR-ALA-ASN-VAL-GLY-LYS-CYS |
| AL-cyc_N08Y | 5 | CKETWTAYVGKC | CYS-LYS-GLU-THR-TRP-THR-ALA-TYR-VAL-GLY-LYS-CYS |
| AL-cyc_G10L | 6 | CKETWTANVLKC | CYS-LYS-GLU-THR-TRP-THR-ALA-ASN-VAL-LEU-LYS-CYS |

Example 4

Screening for Gamma Loop Binding Peptides

Based on the results disclosed in Example 2, the gamma loop peptide was used as a bait to find additional peptides which may positively affect the stability of thrombin. For this purpose, a binding screen was carried out using a fluorescent gamma loop peptide incubated with several peptide arrays.

A library of 1,676 15-meric peptides spanning the sequences of proteins interacting with the gamma loop of thrombin such as thrombin itself, anti-thrombin III (ATIII), thrombomodulin, heparin cofactor II, bovine pancreatic trypsin inhibitor (BPTI), and hirudin, and modifications of the thrombin gamma loop sequence were generated. Peptides were synthesized using SPOT synthesis (Wenschuh H, et al. (2000). Coherent membrane supports for parallel microsynthesis and screening of bioactive peptides. Biopolymers 55:188-206) and were chemoselectively immobilized onto functionalized glass slides as described (Panse S, et al. (2004) Profiling of generic anti-phosphopeptide antisize: 10 μm). Signal intensities were evaluated using spot recognition software GENEPIX® Pro 7.0 analysis software (Molecular Devices). For each peptide, the mean signal intensity of the three triplicates was extracted. Further evaluation and representation of results was performed using the statistical computing and graphics software R (Version 2.11.1, www.r-project.org).

One array included peptides based on the thrombin sequence. Any peptide isolated from this library may reflect possible regions in the thrombin protein that may interact with the gamma loop. A second array was composed of random peptides of which several arbitrarily peptides showed affinity to the gamma loop. The fluorescence for the strongest binding candidates (hits) was quantified on an arbitrary scale of 0-65535 ($2^{16}$). Thrombin activity was assesed as described in Example 1.

The amino acid sequences of the candidate peptides identified in the screen from the thrombin derived peptide array (Thr; SEQ ID NO:7-11) and the random peptide array (Rnd; SEQ ID NO:12-13) are shown in Table 2 herein below:

TABLE 2

| Binding and sequence of different gamma-loop interacting peptides | | | | |
|---|---|---|---|---|
| Peptide | SEQ ID NO: | Sequence (1-letter) | Binding intensity of gamma loop (arbitrary units) | Binding intensity of thrombin (100 μg/ml) |
| Thr_069 | 7 | WCYVAGKPGDFGYCD | 50553 | 3141 |
| Thr_111 | 8 | ISMLEKIYIHPRYNW | 32804 | 60199 |
| Thr_031_CS | 9 | NITRSGIESQLWRSR | 40787 | 18537 |
| Thr_032_CS | 10 | SGIESQLWRSRYPHK | 35117 | 15079 |
| Thr_136_CS | 11 | RIRITDNMFSAGYKP | 25278 | 5535 |
| Rnd_inter_316 | 12 | LGNKKFVSGSRFVST | 26628 | 12353 |
| Rnd_inter_155 | 13 | SHNQRFVTYLGSKLG | 19539 | 23646 |

Underlined and in bold are the S substitutions.

All of these peptides ("mutant gamma loop peptides" identified in Example 3, random peptides, thrombin derived peptides, and "gamma loop binding peptides" mentioned above) were tested for their ability to stabilize thrombin activity at a concentration of 0.5 mM as described in Example 2.

Figure 3A:
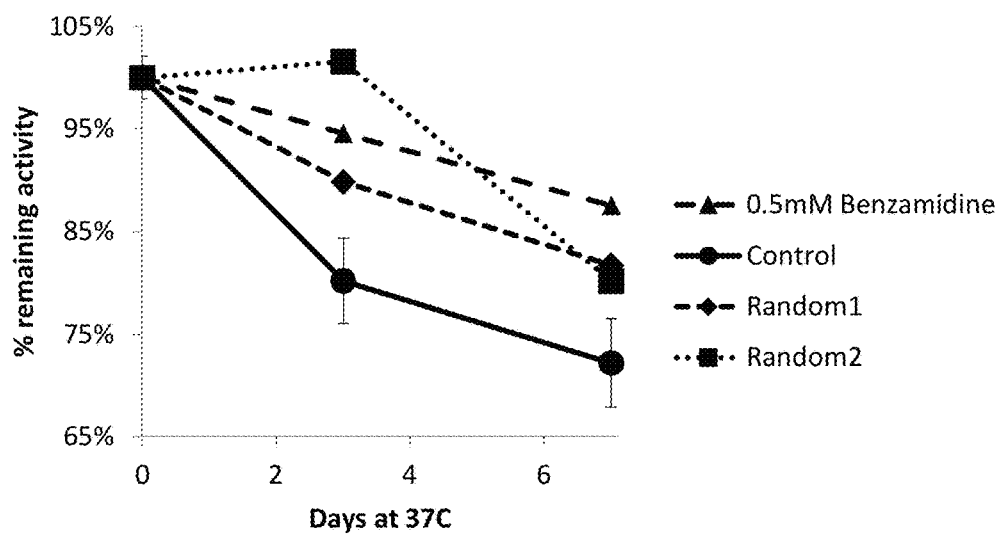
FIGS. 3A-3F are graphs showing stabilization or destabilization level of thrombin by peptides disclosed herein. Thrombin at 1000 IU/ml was incubated with 0.5 mM of the various peptides in vials, as indicated. The remaining activity in the individual vials was measured after incubation at 37° C. for 0, 3 and 7 days. Benzamidine, a direct active site inhibitor of thrombin was used as a control at 0.5 mM. A control group without any peptide or inhibitor additives is also included. The results are divided by groups.

The results are shown in the figures, as follows:

FIG. 3A shows stabilization level of thrombin activity (as % of remaining activity) using random candidate peptide binding to the gamma loop (Random peptides represented by SEQ ID NO:12 and SEQ ID NO:13).

Figure 3B:
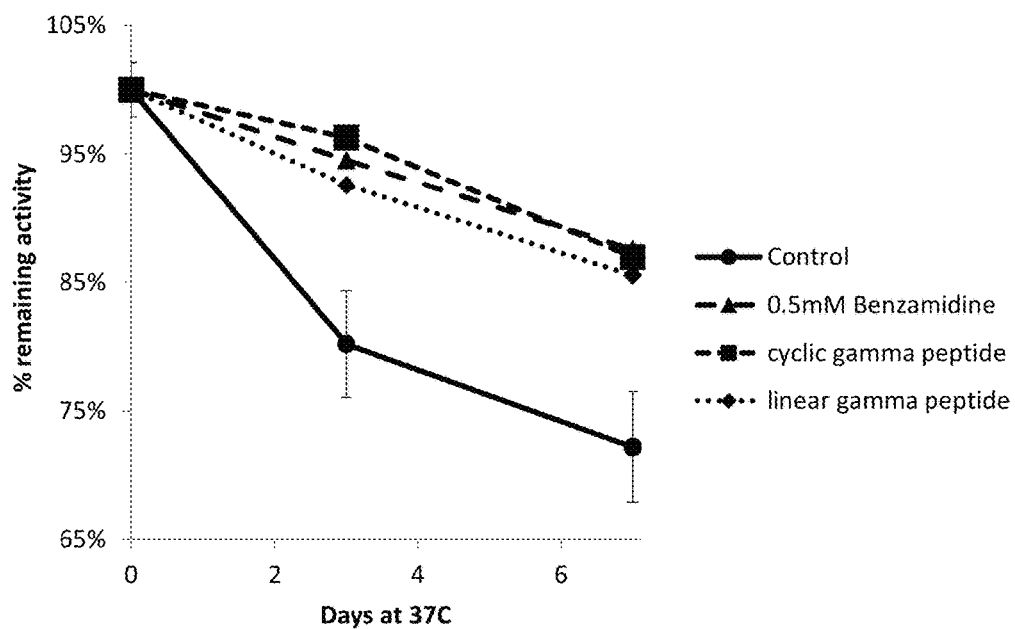

FIG. 3B shows stabilization level of thrombin activity (as % of remaining activity) using peptides comprising the gamma loop sequence, "linear gamma peptide" (SEQ ID NO: 2) and cyclic via intramolecular S—S bonding, "cyclic gamma peptide" ("CS", SEQ ID NO:3).

Figure 3C:
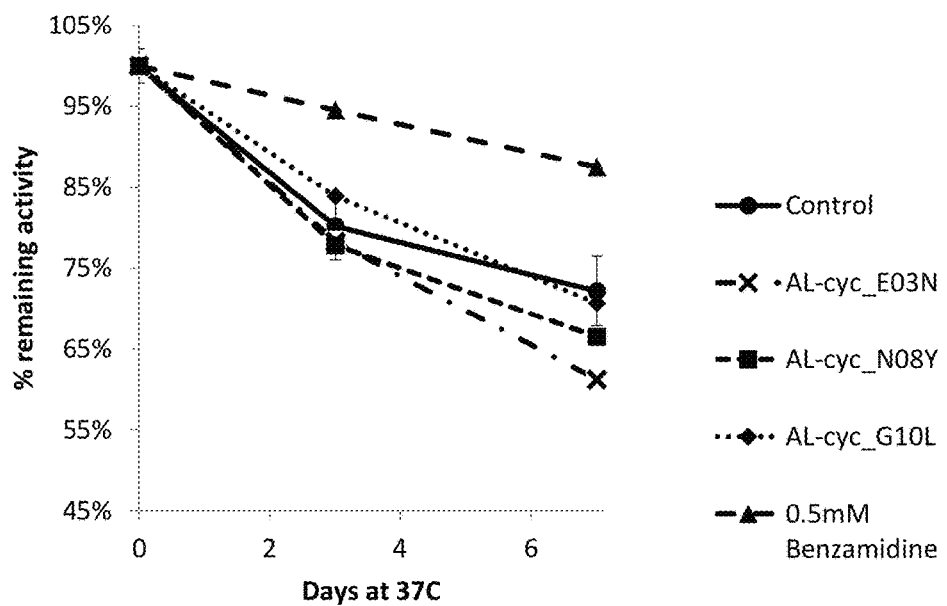

FIG. 3C shows stabilization level of thrombin activity (as % of remaining activity) using gamma loop mutant peptides circularized via intramolecular S—S bonding and displaying an enhanced binding to thrombin.

Figure 3D:
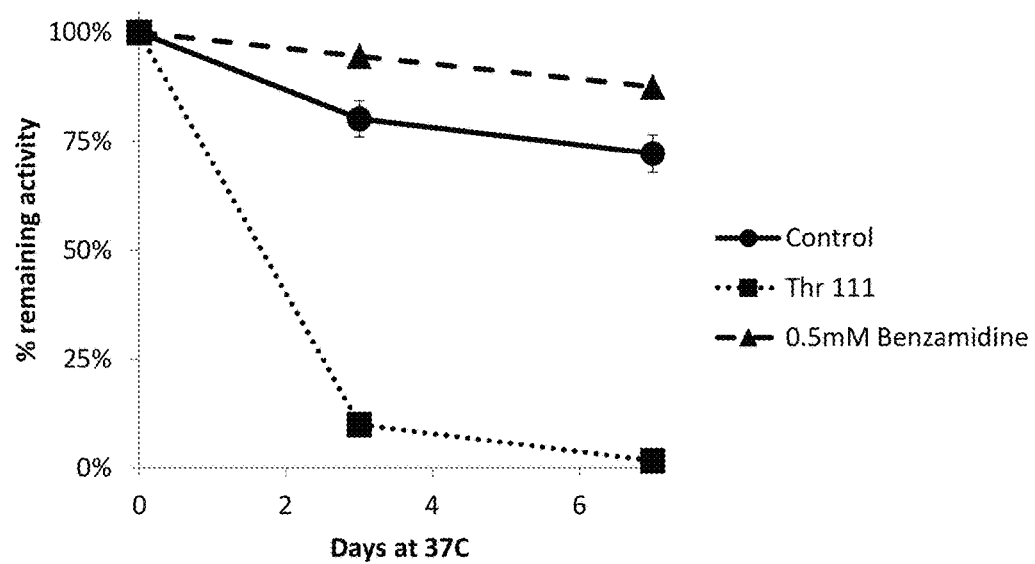

FIG. 3D shows stabilization level of thrombin activity (as % of remaining activity) using the thrombin derived peptide Thr-111 (SEQ ID NO:8). The results show that binding of Thr-111 (SEQ ID NO:8) to thrombin increased thrombin degradation although it did not appear to bind at the active site.

Figure 3E:
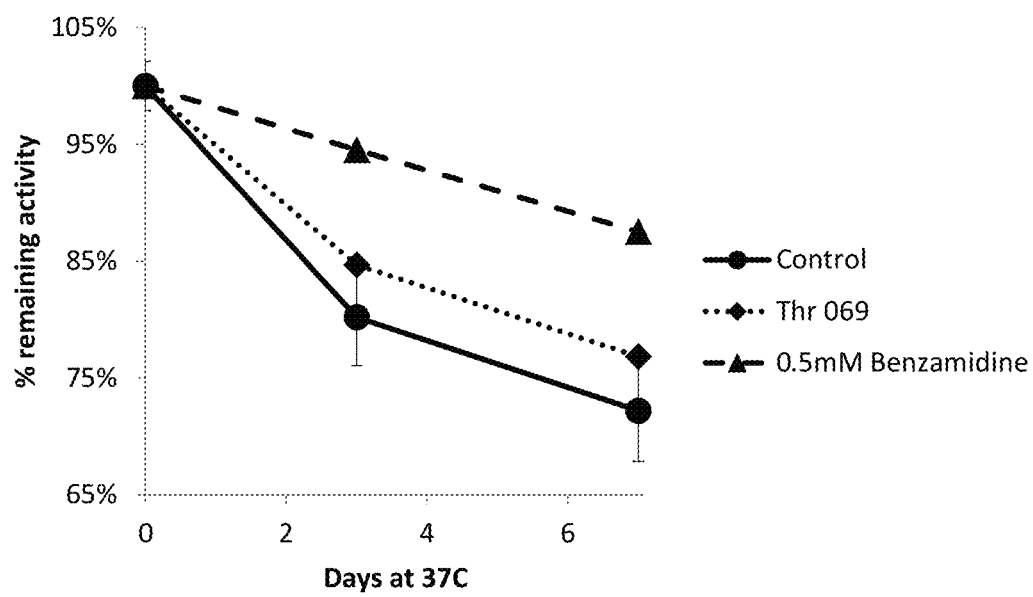

FIG. 3E shows stabilization level of thrombin activity (as % of remaining activity) using thrombin derived peptide Thr-069 (SEQ ID NO:7). The results show that Thr-069 (SEQ ID NO:7 that exhibit very weak binding to thrombin also showed minimal effect on thrombin stability.

Figure 3F:
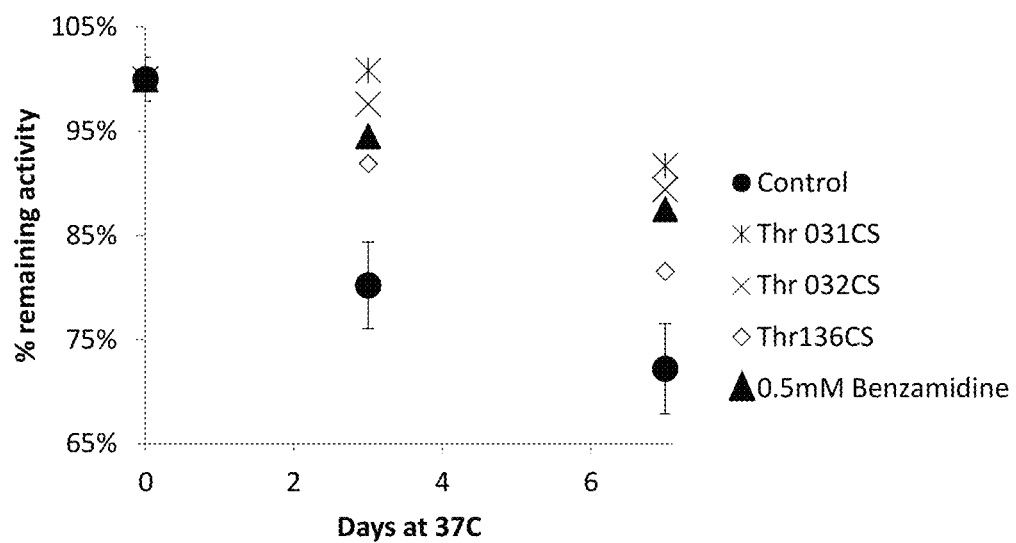

FIG. 3F shows stabilization levels of thrombin (as % of remaining activity) using mutant of thrombin derived peptides in which Cysteine residues have been replaced by Serine residues, displaying variable binding to the gamma loop, and all of which show some reduction in binding when thrombin is inhibited. The amino acid sequences of the thrombin peptides are based on the three dimensional structure of thrombin and do not necessarily include a consecutive sequence of thrombin polypeptide. All three mutants of thrombin derived peptides were capable of stabilizing thrombin. The least effective peptide, Thr-136CS (SEQ ID NO:11), also had the weakest fluorescent signal (Table 2, weakest binding to thrombin).

The data from Table 2 and FIGS. 3A-3F indicate the following:

Peptides comprising the gamma loop sequence (SEQ ID NO:2 and SEQ ID NO:3), whether linear or cyclic, displayed similar and efficient stabilization of thrombin activity (FIG. 3B).

Relatively weak thrombin interacting peptides [such as Thr-069 (SEQ ID NO:7)] and Thr-136CS [SEQ ID NO:11)] exhibited a weaker stabilization effect than similar peptides in the same group (FIGS. 3E and 3F).

Peptide Thr-111 (SEQ ID NO:8), having the strongest interaction with thrombin had a destabilization effect on thrombin (FIG. 3D).

Stabilization of thrombin with cyclic peptides, mutant in residues E, N or G of the gamma loop was inefficient; (SEQ ID NOS: 4, 5, and 6, respectively) (FIG. 3C). Thus, the interaction between the gamma loop peptide and thrombin is specific, and the stabilization effect may be lost if key residues are mutated, even though binding affinity may be increased.

The two random peptides (SEQ ID NOS:12 and 13) both yielded some stabilization effect of thrombin (FIG. 3A). As was described above, these peptides were selected from a random library on the basis of their initial binding to the gamma loop, and this appears to be a good predictor of their stabilizing capacity.

Example 5

Testing Peptides for Thrombin Inhibitory Activity

Peptides that exhibited thrombin stabilization activity were tested for their effect on activity of thrombin toward heterologous substrates.

The assay was carried out as described in Example 1.

FIGS. 4A and B show levels of thrombin inhibition by gamma loop/thrombin gamma binding peptides (the inhibition can be calculated from the % of remaining activity shown in the graph).

FIG. 4A shows two thrombin derived peptides [Thr 031 CS (SEQ ID NO:9)], Thr 032 CS (SEQ ID NO:10)] both of which showed some stabilization effect on thrombin also exhibited an inhibitory effect on thrombin at the same concentrations (e.g. 0.5 mM peptide: 13-14% inhibition). At higher peptide concentrations (1 mM) the inhibition was greater than 30%. The cyclic gamma peptide (SEQ ID NO:3) showed only ~7% inhibition of thrombin at 0.5 mM, while the linear gamma peptide (SEQ ID NO:1) exhibited about 20% inhibition (FIG. 2D). Both peptides displayed a similar stabilizing effect of thrombin at this concentration. Peptide Rnd 316 (SEQ ID NO:12) showed absolutely no inhibition of thrombin activity at any concentration tested.

Benzamidine at the same concentration (0.5 mM) showed 20% inhibition in this assay, which was higher than any of the peptides tested.

These data demonstrate that it is possible to use specific peptides for stabilizing thrombin without compromising thrombin activity (in contrast to the use of benzamidine).

Figure 4A:
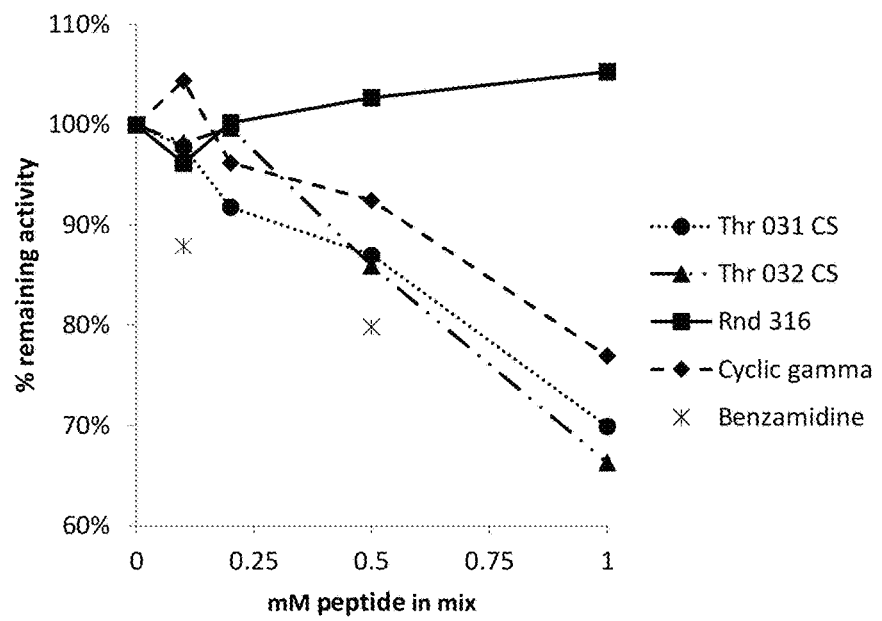
FIGS. 4A and 4B show levels of thrombin inhibition (%) by gamma loop/binding peptides (the inhibition can be calculated from the % of remaining activity shown in the graph): thrombin derived peptides (Thr 031 CS [SEQ ID NO:9], Thr 032 CS [SEQ ID NO:10]); cyclic gamma peptide [SEQ ID NO:3]; Peptide Rnd 316 [SEQ ID NO:12], and linear gamma peptide [SEQ ID NO:1].
Figure 4B:
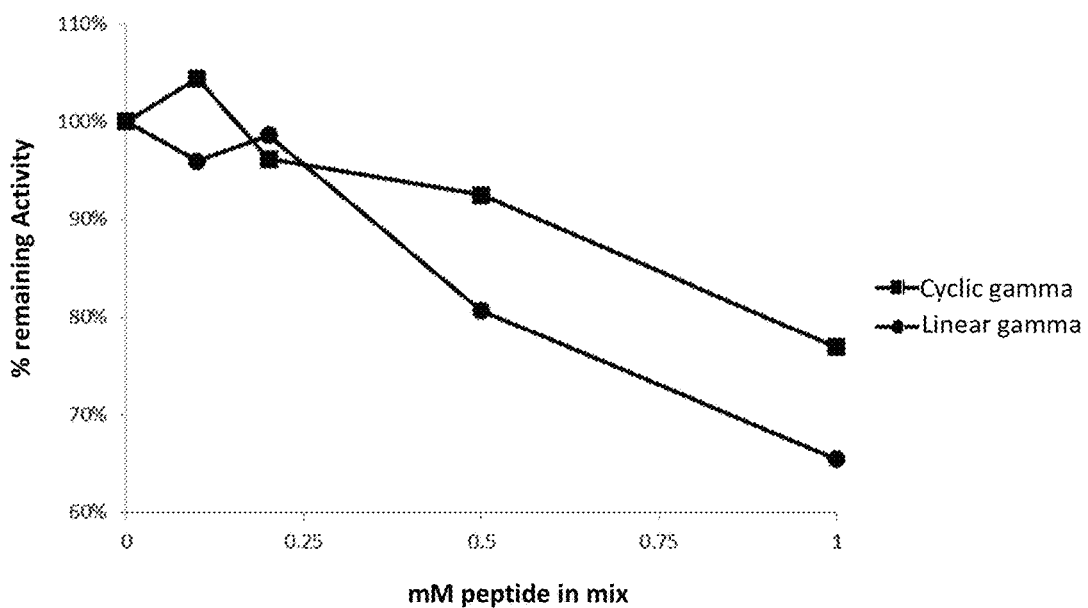

FIG. 4B shows inhibition of thrombin (the inhibition can be calculated from the % of remaining activity shown in the graph) by the linear (SEQ ID NO:1) and cyclic (SEQ ID NO:3) thrombin gamma loop peptides.

The cyclic gamma peptide (SEQ ID NO:3) showed only ~7% inhibition at 0.5 mM, and the linear gamma peptide (SEQ ID NO:1) exhibited about 20% inhibition. Both peptides displayed a similar stabilizing effect of thrombin at this concentration.

In summary, and without wishing to be bound to theory, three categories of peptides are shown to stabilize thrombin:

1) A linear or cyclic (i.e. intramolecular S-S bonds) gamma loop peptide or linear or cyclic peptide which contains the consecutive amino acid sequence of the thrombin gamma loop;

2) Peptides selected from molecules known to interact with thrombin, such as thrombin itself but may also include anti-thrombin III, thrombomodulin or others, that show binding to the gamma loop;

3) Randomly selected peptides that show a binding interaction with the gamma loop.

In general, the above peptides do not inhibit thrombin at the same concentrations at which they stabilize it. Thrombin is active yet stable, thus, these peptides can be used to stabilize thrombin activity in the liquid formulation thereby retaining its activity toward heterologous substrates.

Although various embodiments have been described herein, many modifications and variations to those embodiments may be implemented. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference.

Citation or identification of any reference in this application shall not be construed as an admission that such reference is available as prior art to the invention.

Section headings are used herein to ease understanding of the specification and should not be construed as necessarily limiting.

We claim:

1. A stabilized thrombin pharmaceutical composition comprising: thrombin in a pharmacologically acceptable aqueous liquid excipient and an isolated peptide having at least 10 amino acid residues in length or a salt thereof, wherein said isolated peptide or salt thereof comprises the amino acid sequence of the gamma loop interacting peptide selected from the group consisting of amino acid sequences of SEQ ID NO: 9, 10, 11, 12 and 13.

2. A stabilized thrombin formulation comprising: thrombin in a pharmacologically acceptable aqueous liquid excipient and an isolated peptide or a salt thereof, wherein said isolated peptide or salt thereof comprises the amino acid sequence of a gamma loop interacting peptide selected from the group consisting of amino acid sequences of SEQ ID NO: 9, 10, 11, 12 and 13.

3. The formulation of claim 2 having a thrombin activity of about 1 IU/ml to 10,000 IU/ml.

4. The formulation of claim 2 having a thrombin activity of about 10 IU/ml to 5,000 IU/ml.

5. The formulation of claim 2 having a thrombin activity of about 10 IU/ml to 1,000 IU/ml.

6. The formulation of claim 2, wherein the peptide is present at a concentration of about 0.01 mM to 1 mM.

7. The formulation of claim 6, wherein the peptide is present at a concentration of about 0.1 mM to 0.5 mM.

8. The formulation of claim 6, wherein the peptide is present at a concentration of about 0.5 mM.

9. The formulation of claim 2 for use as a fibrin sealant component.

10. The composition of claim 1 or the formulation of claim 2 contained in a sealed container having a label affixed to an exterior surface thereof.

* * * * *

SEQUENCE LISTING

```
<160> NUMBER OF SEQ ID NOS: 13

<210> SEQ ID NO 1
<211> LENGTH: 10
<212> TYPE: PRT
<213> ORGANISM: ARTIFICIAL
<220> FEATURE:
<223> OTHER INFORMATION: Synthetic peptide

<400> SEQUENCE: 1

Lys Glu Thr Trp Thr Ala Asn Val Gly Lys
1               5                   10

<210> SEQ ID NO 2
<211> LENGTH: 17
<212> TYPE: PRT
<213> ORGANISM: ARTIFICIAL
<220> FEATURE:
<223> OTHER INFORMATION: Synthetic peptide

<400> SEQUENCE: 2

Gly Asn Leu Lys Glu Thr Trp Thr Ala Asn Val Gly Lys Gly Gln Pro
1               5                   10                  15

Ser

<210> SEQ ID NO 3
<211> LENGTH: 12
<212> TYPE: PRT
<213> ORGANISM: ARTIFICIAL
<220> FEATURE:
<223> OTHER INFORMATION: Synthetic peptide

<400> SEQUENCE: 3

Cys Lys Glu Thr Trp Thr Ala Asn Val Gly Lys Cys
1               5                   10
```

<210> SEQ ID NO 4
<211> LENGTH: 12
<212> TYPE: PRT
<213> ORGANISM: ARTIFICIAL
<220> FEATURE:
<223> OTHER INFORMATION: Synthetic peptide

<400> SEQUENCE: 4

Cys Lys Asn Thr Trp Thr Ala Asn Val Gly Lys Cys
1               5                   10

<210> SEQ ID NO 5
<211> LENGTH: 12
<212> TYPE: PRT
<213> ORGANISM: ARTIFICIAL
<220> FEATURE:
<223> OTHER INFORMATION: Synthetic peptide

<400> SEQUENCE: 5

Cys Lys Glu Thr Trp Thr Ala Tyr Val Gly Lys Cys
1               5                   10

<210> SEQ ID NO 6
<211> LENGTH: 12
<212> TYPE: PRT
<213> ORGANISM: ARTIFICIAL
<220> FEATURE:
<223> OTHER INFORMATION: Synthetic peptide

<400> SEQUENCE: 6

Cys Lys Glu Thr Trp Thr Ala Asn Val Leu Lys Cys
1               5                   10

<210> SEQ ID NO 7
<211> LENGTH: 15
<212> TYPE: PRT
<213> ORGANISM: ARTIFICIAL
<220> FEATURE:
<223> OTHER INFORMATION: Synthetic peptide

<400> SEQUENCE: 7

Trp Cys Tyr Val Ala Gly Lys Pro Gly Asp Phe Gly Tyr Cys Asp
1               5                   10                  15

<210> SEQ ID NO 8
<211> LENGTH: 15
<212> TYPE: PRT
<213> ORGANISM: ARTIFICIAL
<220> FEATURE:
<223> OTHER INFORMATION: Synthetic peptide

<400> SEQUENCE: 8

Ile Ser Met Leu Glu Lys Ile Tyr Ile His Pro Arg Tyr Asn Trp
1               5                   10                  15

<210> SEQ ID NO 9
<211> LENGTH: 15
<212> TYPE: PRT
<213> ORGANISM: ARTIFICIAL
<220> FEATURE:
<223> OTHER INFORMATION: Synthetic peptide

<400> SEQUENCE: 9

Asn Ile Thr Arg Ser Gly Ile Glu Ser Gln Leu Trp Arg Ser Arg
1               5                   10                  15

```
<210> SEQ ID NO 10
<211> LENGTH: 15
<212> TYPE: PRT
<213> ORGANISM: ARTIFICIAL
<220> FEATURE:
<223> OTHER INFORMATION: Synthetic peptide

<400> SEQUENCE: 10

Ser Gly Ile Glu Ser Gln Leu Trp Arg Ser Arg Tyr Pro His Lys
1               5                   10                  15

<210> SEQ ID NO 11
<211> LENGTH: 15
<212> TYPE: PRT
<213> ORGANISM: ARTIFICIAL
<220> FEATURE:
<223> OTHER INFORMATION: Synthetic peptide

<400> SEQUENCE: 11

Arg Ile Arg Ile Thr Asp Asn Met Phe Ser Ala Gly Tyr Lys Pro
1               5                   10                  15

<210> SEQ ID NO 12
<211> LENGTH: 15
<212> TYPE: PRT
<213> ORGANISM: ARTIFICIAL
<220> FEATURE:
<223> OTHER INFORMATION: Synthetic peptide

<400> SEQUENCE: 12

Leu Gly Asn Lys Lys Phe Val Ser Gly Ser Arg Phe Val Ser Thr
1               5                   10                  15

<210> SEQ ID NO 13
<211> LENGTH: 15
<212> TYPE: PRT
<213> ORGANISM: ARTIFICIAL
<220> FEATURE:
<223> OTHER INFORMATION: Synthetic peptide

<400> SEQUENCE: 13

Ser His Asn Gln Arg Phe Val Thr Tyr Leu Gly Ser Lys Leu Gly
1               5                   10                  15
```